US011259866B2

(12) United States Patent
Germain et al.

(10) Patent No.: US 11,259,866 B2
(45) Date of Patent: Mar. 1, 2022

(54) TISSUE EXTRACTION DEVICES AND METHODS

(71) Applicant: MINERVA SURGICAL, INC., Santa Clara, CA (US)

(72) Inventors: Aaron Germain, Campbell, CA (US); Kyle Klein, San Jose, CA (US); Michael D. Walker, San Francisco, CA (US); Benedek Orczy-Timko, Budapest (HU)

(73) Assignee: MINERVA SURGICAL, INC., Santa Clara, CA (US)

( * ) Notice: Subject to any disclaimer, the term of this patent is extended or adjusted under 35 U.S.C. 154(b) by 185 days.

(21) Appl. No.: 16/800,359

(22) Filed: Feb. 25, 2020

(65) Prior Publication Data
US 2020/0246067 A1    Aug. 6, 2020

Related U.S. Application Data

(63) Continuation of application No. 15/660,466, filed on Jul. 26, 2017, now Pat. No. 10,603,104, which is a continuation of application No. 15/205,178, filed on Jul. 8, 2016, now Pat. No. 9,743,979, which is a continuation of application No. 13/599,928, filed on Aug. 30, 2012, now Pat. No. 9,439,720.

(60) Provisional application No. 61/556,646, filed on Nov. 7, 2011, provisional application No. 61/541,803, filed on Sep. 30, 2011, provisional application No. 61/538,588, filed on Sep. 23, 2011, provisional application No. 61/534,256, filed on Sep. 13, 2011,
(Continued)

(51) Int. Cl.
*A61B 17/32* (2006.01)
*A61B 18/14* (2006.01)
*A61B 18/18* (2006.01)
*A61B 90/30* (2016.01)
*A61B 18/04* (2006.01)
*A61B 18/00* (2006.01)

(52) U.S. Cl.
CPC ........ *A61B 18/1485* (2013.01); *A61B 18/042* (2013.01); *A61B 18/18* (2013.01); *A61B 90/30* (2016.02); *A61B 2018/00083* (2013.01); *A61B 2018/00559* (2013.01); *A61B 2018/00601* (2013.01); *A61B 2018/00982* (2013.01); *A61B 2018/142* (2013.01); *A61B 2218/002* (2013.01); *A61B 2218/007* (2013.01)

(58) Field of Classification Search
CPC . A61B 18/1485; A61B 18/18; A61B 19/5202; A61B 2018/00559; A61B 2018/00601; A61B 2018/00982; A61B 2218/002; A61B 2218/007
See application file for complete search history.

(56) References Cited

U.S. PATENT DOCUMENTS 3,850,162 A    11/1974  Iglesias
3,945,375 A     3/1976  Banko
(Continued)

FOREIGN PATENT DOCUMENTS

WO    2010127174 A1    11/2010

*Primary Examiner* — Rex R Holmes
(74) *Attorney, Agent, or Firm* — Seager, Tufte & Wickhem, LLP

(57) ABSTRACT

A tissue resection device comprises inner and outer coaxial sleeves. The outer sleeve has a cutting window formed therein, and the inner sleeve has a distal cutting end that can be reciprocated past the cutting window. The sleeves comprise electrodes to provide electrosurgical cutting, and an edge portion of the window includes a dielectric material.

20 Claims, 21 Drawing Sheets

Related U.S. Application Data provisional application No. 61/530,314, filed on Sep. 1, 2011.

(56) References Cited

U.S. PATENT DOCUMENTS

| | | |
|---|---|---|
| 4,203,444 A | 5/1980 | Bonnell et al. |
| 4,369,768 A | 1/1983 | Vukovic |
| 4,606,330 A | 8/1986 | Bonnet |
| 4,955,882 A | 9/1990 | Hakky |
| 4,998,527 A | 3/1991 | Meyer |
| 5,009,656 A | 4/1991 | Reimels |
| 5,106,364 A | 4/1992 | Hayafuji et al. |
| 5,169,397 A | 12/1992 | Sakashita et al. |
| 5,195,541 A | 3/1993 | Obenchain |
| 5,217,479 A | 6/1993 | Shuler |
| 5,312,399 A | 5/1994 | Hakky et al. |
| 5,320,091 A | 6/1994 | Grossi et al. |
| 5,456,689 A | 10/1995 | Kresch et al. |
| 5,527,331 A | 6/1996 | Kresch et al. |
| 5,697,281 A | 12/1997 | Eggers et al. |
| 5,730,752 A | 3/1998 | Alden et al. |
| 5,759,185 A | 6/1998 | Grinberg |
| 5,873,886 A | 2/1999 | Larsen et al. |
| 5,885,277 A | 3/1999 | Korth |
| 5,906,615 A | 5/1999 | Thompson |
| 5,941,876 A | 8/1999 | Nardella et al. |
| 5,997,534 A | 12/1999 | Tu et al. |
| 6,004,319 A | 12/1999 | Goble et al. |
| 6,024,751 A | 2/2000 | Lovato et al. |
| 6,032,673 A | 3/2000 | Savage et al. |
| 6,056,746 A | 5/2000 | Goble et al. |
| 6,090,106 A | 7/2000 | Goble et al. |
| 6,113,594 A | 9/2000 | Savage |
| 6,149,620 A | 11/2000 | Baker et al. |
| 6,159,160 A | 12/2000 | Hsei et al. |
| 6,245,084 B1 | 6/2001 | Mark et al. |
| 6,293,942 B1 | 9/2001 | Goble et al. |
| 6,358,263 B2 | 3/2002 | Mark et al. |
| 6,832,996 B2 | 12/2004 | Woloszko et al. |
| 6,979,332 B2 | 12/2005 | Adams |
| 7,226,459 B2 | 6/2007 | Cesarini et al. |
| 7,244,256 B2 | 7/2007 | DeCesare et al. |
| 7,249,602 B1 | 7/2007 | Emanuel |
| 7,678,070 B2 | 3/2010 | Kumar et al. |
| 7,901,403 B2 | 3/2011 | Woloszko et al. |
| 7,918,822 B2 | 4/2011 | Kumar et al. |
| 8,061,359 B2 | 11/2011 | Emanuel |
| 8,226,549 B2 | 7/2012 | Kumar et al. |
| 8,267,934 B2 | 9/2012 | Earley et al. |
| 8,308,726 B2 | 11/2012 | Kumar et al. |
| 8,388,570 B2 | 3/2013 | Kumar et al. |
| 8,460,178 B2 | 6/2013 | Kumar et al. |
| 8,512,283 B2 | 8/2013 | Kumar et al. |
| 8,512,326 B2 | 8/2013 | Shadduck et al. |
| 8,568,424 B2 | 10/2013 | Shugrue et al. |
| 8,574,253 B2 | 11/2013 | Gruber et al. |
| 8,591,464 B2 | 11/2013 | Kumar et al. |
| 8,652,089 B2 | 2/2014 | Kumar et al. |
| 8,663,216 B2 | 3/2014 | Davison et al. |
| 8,840,625 B2 | 9/2014 | Adams et al. |
| 8,840,626 B2 | 9/2014 | Adams et al. |
| 8,893,722 B2 | 11/2014 | Emanuel |
| 8,951,274 B2 | 2/2015 | Adams et al. |
| 8,974,448 B2 | 3/2015 | Germain et al. |
| 9,233,193 B2 | 1/2016 | Truckai et al. |
| 9,254,142 B2 | 2/2016 | Germain et al. |
| 2002/0087151 A1 | 7/2002 | Mody |
| 2004/0230190 A1 | 11/2004 | Dahla et al. |
| 2006/0047240 A1 | 3/2006 | Kumar et al. |
| 2006/0122556 A1 | 6/2006 | Kumar et al. |
| 2006/0122557 A1 | 6/2006 | Kumar et al. |
| 2007/0021713 A1 | 1/2007 | Kumar et al. |
| 2008/0021447 A1 | 1/2008 | Davison et al. |
| 2008/0051708 A1 | 2/2008 | Kumar et al. |
| 2008/0058588 A1 | 3/2008 | Emanuel |
| 2008/0058842 A1 | 3/2008 | Emanuel |
| 2008/0091071 A1 | 4/2008 | Kumar et al. |
| 2008/0091074 A1 | 4/2008 | Kumar et al. |
| 2008/0097468 A1 | 4/2008 | Adams et al. |
| 2008/0097471 A1 | 4/2008 | Adams et al. |
| 2008/0249366 A1 | 10/2008 | Gruber et al. |
| 2008/0249553 A1 | 10/2008 | Gruber et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2012/0010464 A1 | 1/2012 | Adams et al. |
| 2012/0172888 A1 | 7/2012 | Shugrue et al. |
| 2012/0172889 A1 | 7/2012 | Chin et al. |
| 2012/0197280 A1 | 8/2012 | Emanuel |
| 2012/0271110 A1 | 10/2012 | Kumar et al. |
| 2013/0046316 A1 | 2/2013 | Sullivan et al. |
| 2013/0103021 A1 | 4/2013 | Germain et al. |
| 2013/0172870 A1 | 7/2013 | Germain et al. |
| 2014/0074136 A1 | 3/2014 | Emanuel |
| 2015/0012023 A1 | 1/2015 | Emanuel |

TISSUE EXTRACTION DEVICES AND METHODS

CROSS-REFERENCE TO RELATED APPLICATIONS

This application is a continuation of U.S. application Ser. No. 15/660,466, filed Jul. 26, 2017, which is a continuation of U.S. application Ser. No. 15/205,178, filed Jul. 8, 2016, now U.S. Pat. No. 9,743,979, which is a continuation of U.S. application Ser. No. 13/599,928, filed Aug. 30, 2012, now U.S. Pat. No. 9,439,720, which claims priority to U.S. Provisional Application No. 61/530,314, filed Sep. 1, 2011; U.S. Provisional Application No. 61/534,256, filed Sep. 13, 2011; U.S. Provisional Application No. 61/538,588, filed Sep. 23, 2011; U.S. Provisional Application No. 61/541,803, filed Sep. 30, 2011; and U.S. Provisional Application No. 61/556,646, filed Nov. 7, 2011; the entire contents of which are incorporated herein by reference.

FIELD OF THE INVENTION

The present invention relates systems and methods for the cutting and extraction of uterine fibroid tissue, polyps and other abnormal uterine tissue.

BACKGROUND OF THE INVENTION

Uterine fibroids are non-cancerous tumors that develop in the wall of uterus. Such fibroids occur in a large percentage of the female population, with some studies indicating up to 40 percent of all women have fibroids. Uterine fibroids can grow over time to be several centimeters in diameter and symptoms can include menorrhagia, reproductive dysfunction, pelvic pressure and pain.

One current treatment of fibroids is hysteroscopic resection or myomectomy which involves transcervical access to the uterus with a hysteroscope together with insertion of a cutting instrument through a working channel in the hysteroscope. The cutting instrument may be a mechanical tissue cutter or an electrosurgical resection device such as a cutting loop. Mechanical cutting devices are disclosed in U.S. Pat. Nos. 7,226,459; 6,032,673 and 5,730,752 and U.S. Published Patent Appl. 2009/0270898. An electrosurgical cutting device is disclosed in U.S. Pat. No. 5,906,615.

Electrosurgical cutting devices having inner and outer tubes with a cutting window in the outer sleeve are described in commonly owned application Ser. Nos. 13/531,309; 13/277,913; 13/442,686; and Ser. No. 13/534,980, the full disclosures of which are incorporated herein by reference.

While hysteroscopic resection can be effective in removing uterine fibroids, many commercially available instrument are too large in diameter and thus require anesthesia in an operating room environment. Conventional resectoscopes require cervical dilation to about 9 mm. What is needed is a system that can effectively cut and remove fibroid tissue through a small diameter hysteroscope.

SUMMARY OF THE INVENTION

The present invention provides improvement electrosurgical cutting devices comprising an outer tube and an inner tube reciprocatably disposed in a central lumen or passage of the outer tube. The tubes are each formed from or include electrically conductive materials so that they act as the electrodes of the electrosurgical cutting device when connected to opposite poles of an electrosurgical power supply.

In accordance with the present invention, a dielectric material is disposed over or incorporated into a structure circumscribing the cutting window or the outer tube. The dimensions and geometry of the dielectric structure are chosen to optimize plasma generation about a cutting end or electrode at a distal end of the inner electrode as the inner electrode is advanced (with radiofrequency energy being applied) past the cutting window with tissue invaginated within the window.

DETAILED DESCRIPTION

Figure 1:
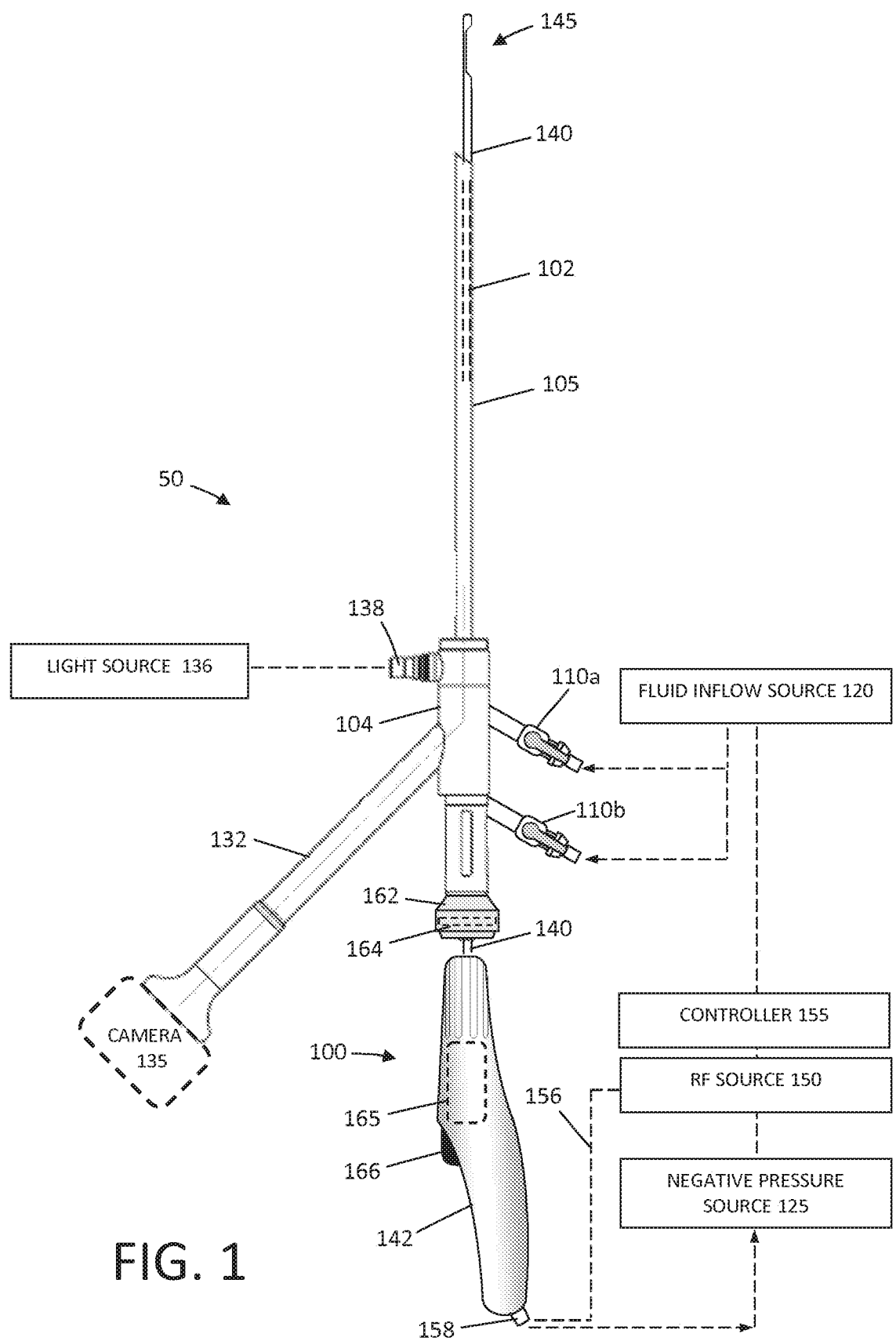
FIG. 1 is a plan view of an assembly including a hysteroscope and a tissue-cutting device corresponding to the invention that is inserted through the working channel of the hysteroscope.
Figure 2:
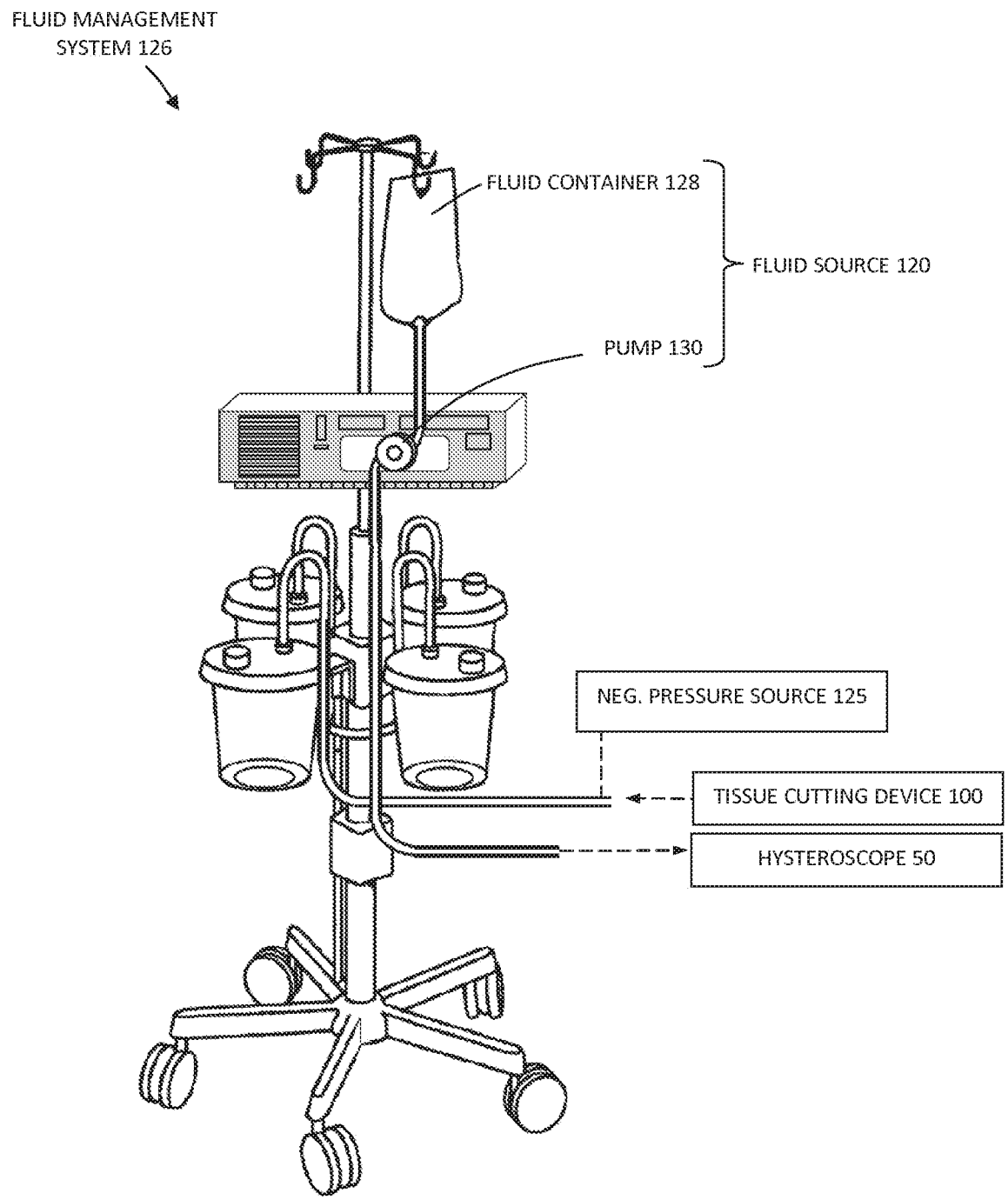
FIG. 2 is a schematic perspective view of a fluid management system used for distending the uterus and for assisting in electrosurgical tissue cutting and extraction.
Figure 3:
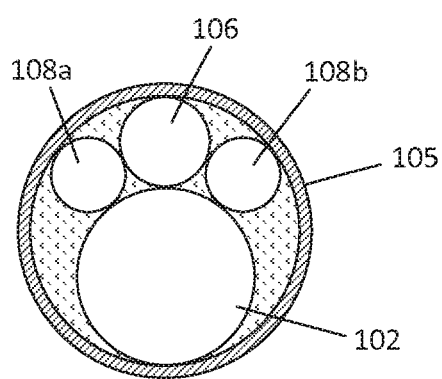
FIG. 3 is a cross-sectional view of the shaft of the hysteroscope of FIG. 1 showing various channels therein.

FIG. 1 illustrates an assembly that comprises an endoscope 50 used for hysteroscopy together with a tissue-extraction device 100 extending through a working channel 102 of the endoscope. The endoscope or hysteroscope 50 has a handle 104 coupled to an elongated shaft 105 having a diameter of 5 mm to 7 mm. The working channel 102 therein may be round, D-shaped or any other suitable shape. The endoscope shaft 105 is further configured with an optics channel 106 and one or more fluid inflow/outflow channels 108a, 108b (FIG. 3) that communicate with valve-connectors 110a, 110b configured for coupling to a fluid inflow source 120 thereto, or optionally a negative pressure source 125 (FIGS. 1-2). The fluid inflow source 120 is a component of a fluid management system 126 as is known in the art (FIG. 2) which comprises a fluid container 128 and pump mechanism 130 which pumps fluid through the hysteroscope 50 into the uterine cavity. As can be seen in FIG. 2, the fluid management system 126 further includes the negative pressure source 125 (which can comprise an operating room wall suction source) coupled to the tissue-cutting device 100. The handle 104 of the endoscope includes the angled extension portion 132 with optics to which a videoscopic camera 135 can be operatively coupled. A light source 136 also is coupled to light coupling 138 on the handle of the hysteroscope 50. The working channel 102 of the hysteroscope is configured for insertion and manipulation of the tissue-cutting and extracting device 100, for example to treat and remove fibroid tissue. In one embodiment, the hysteroscope shaft 105 has an axial length of 21 cm, and can comprise a 0° scope, or 15° to 30° scope.

Still referring to FIG. 1, the tissue-cutting device 100 has a highly elongated shaft assembly 140 configured to extend through the working channel 102 in the hysteroscope. A handle 142 of the tissue-cutting device 100 is adapted for manipulating the electrosurgical working end 145 of the device. In use, the handle 142 can be manipulated both rotationally and axially, for example, to orient the working end 145 to cut targeted fibroid tissue. The tissue-cutting device 100 has subsystems coupled to its handle 142 to enable electrosurgical cutting of targeted tissue. A radio frequency generator or RF source 150 and controller 155 are coupled to at least one RF electrode carried by the working end 145 as will be described in detail below. In one embodiment shown in FIG. 1, an electrical cable 156 and negative pressure source 125 are operatively coupled to a connector 158 in handle 142. The electrical cable couples the RF source 150 to the electrosurgical working end 145. The negative pressure source 125 communicates with a tissue-extraction channel 160 in the shaft assembly 140 of the tissue extraction device 100 (FIG. 4).

FIG. 1 further illustrates a seal housing 162 that carries a flexible seal 164 carried by the hysteroscope handle 104 for sealing the shaft 140 of the tissue-cutting device 100 in the working channel 102 to prevent distending fluid from escaping from a uterine cavity.

In one embodiment as shown in FIG. 1, the handle 142 of tissue-cutting device 100 includes a motor drive 165 for reciprocating or otherwise moving a cutting component of the electrosurgical working end 145 as will be described below. The handle 142 optionally includes one or more actuator buttons 166 for actuating the device. In another embodiment, a footswitch can be used to operate the device. In one embodiment, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating cutting sleeve in a non-extended position and in an extended position. Further, the system can include a mechanism for actuating a single reciprocating stroke.

Figure 4:
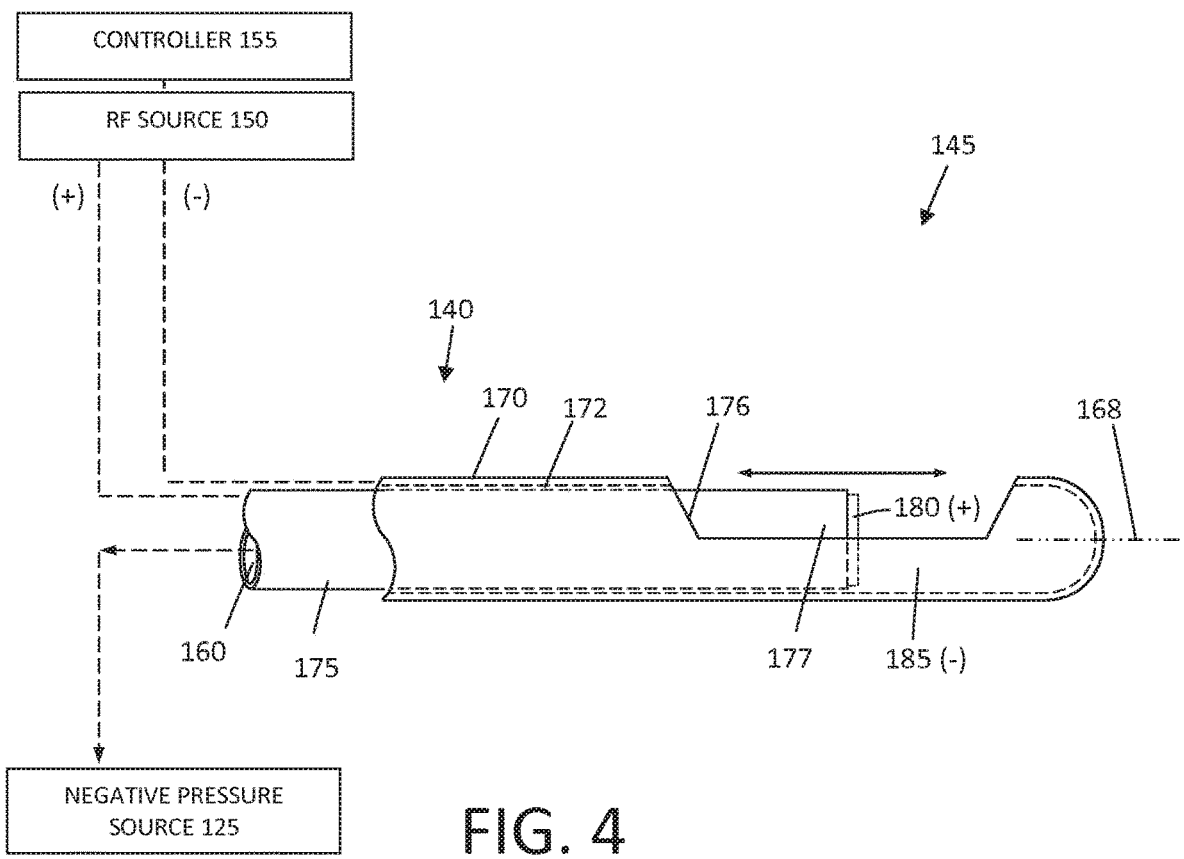
FIG. 4 is a schematic side view of the working end of the electrosurgical tissue-cutting device of FIG. 1 showing an outer sleeve and a reciprocating inner sleeve and an electrode arrangement.

Referring to FIGS. 1 and 4, an electrosurgical tissue-cutting device has an elongate shaft assembly 140 extending about longitudinal axis 168 comprising an exterior or first outer sleeve 170 with passageway or lumen 172 therein that accommodates a second or inner sleeve 175 that can reciprocate (and optionally rotate or oscillate) in lumen 172 to cut tissue as is known in that art of such tubular cutters. In one embodiment, the tissue-receiving window 176 in the outer sleeve 170 has an axial length ranging between 10 mm and 30 mm and extends in a radial angle about outer sleeve 170 from about 45° to 210° relative to axis 168 of the sleeve. The outer and inner sleeves 170 and 175 can comprise a thin-wall stainless steel material and function as opposing polarity electrodes as will be described in detail below. FIGS. 6A-8 illustrate insulative layers carried by the outer and inner sleeves 170 and 175 to limits, control and/or prevent unwanted electrical current flows between certain portions go the sleeve. In one embodiment, a stainless steel outer sleeve 170 has an O.D. of 0.143" with an I.D. of 0.133" and with an inner insulative layer (described below) the sleeve has a nominal I.D. of 0.125". In this embodiment, the stainless steel inner sleeve 175 has an O.D. of 0.120" with an I.D. of 0.112". The inner sleeve 175 with an outer insulative layer has a nominal O.D. of about 0.123" to 0.124" to reciprocate in lumen 172. In other embodiments, outer and or inner sleeves can be fabricated of metal, plastic, ceramic of a combination thereof. The cross-section of the sleeves can be round, oval or any other suitable shape.

As can be seen in FIG. 4, the distal end 177 of inner sleeve 175 comprises a first polarity electrode with distal cutting electrode edge 180 about which plasma can be generated. The electrode edge 180 also can be described as an active electrode during tissue cutting since the electrode edge 180 then has a substantially smaller surface area than the opposing polarity or return electrode. In one embodiment in FIG. 4, the exposed surfaces of outer sleeve 170 comprises the second polarity electrode 185, which thus can be described as the return electrode since during use such an electrode surface has a substantially larger surface area compared to the functionally exposed surface area of the active electrode edge 180.

Figure 5:
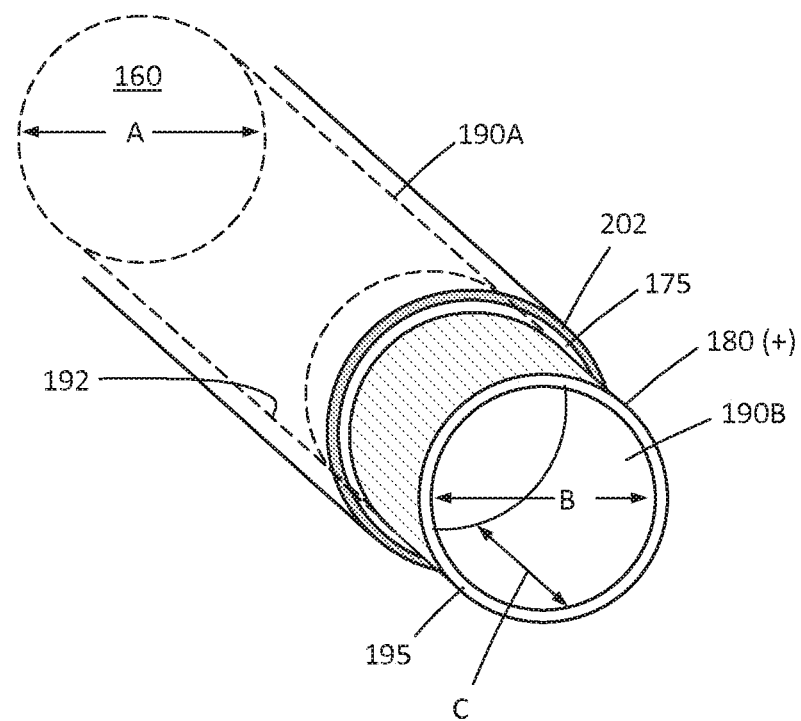
FIG. 5 is a schematic perspective view of the working end of the inner sleeve of FIG. 4 showing its electrode edge.
Figure 6A:
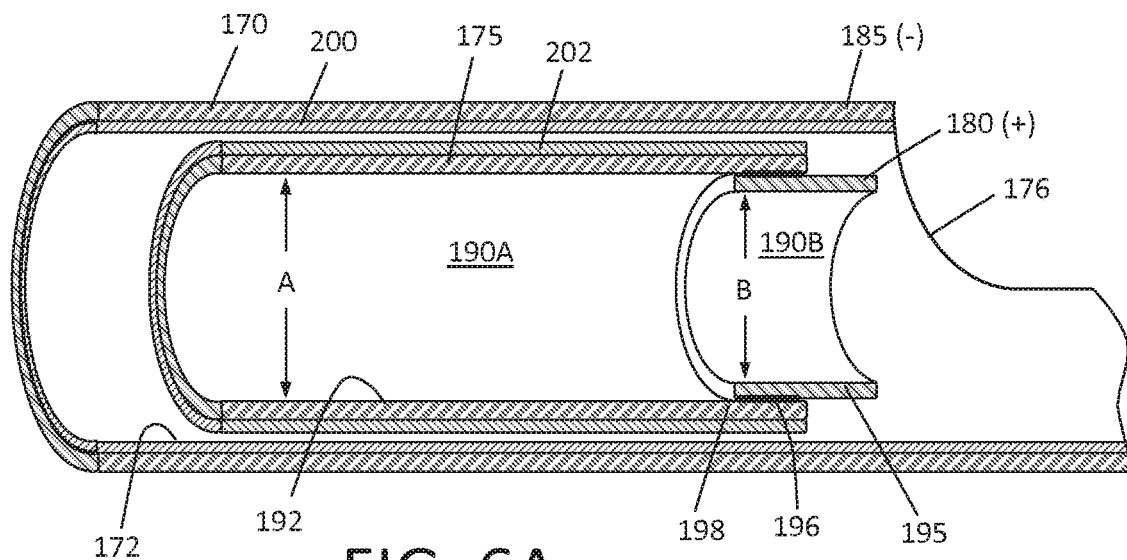
FIG. 6A is a schematic cut-away view of a portion of outer sleeve, inner RF cutting sleeve and a tissue-receiving window of the outer sleeve.

In one aspect of the invention, the inner sleeve or cutting sleeve 175 has an interior tissue extraction lumen 160 with first and second interior diameters that are adapted to electrosurgically cut tissue volumes rapidly—and thereafter consistently extract the cut tissue strips through the highly elongated lumen 160 without clogging. Now referring to FIGS. 5 and 6A, it can be seen that the inner sleeve 175 has a first diameter portion 190A that extends from the handle 142 (FIG. 1) to a distal region 192 of the sleeve 175 wherein the tissue extraction lumen transitions to a smaller second diameter lumen 190B with a reduced diameter indicated at B which is defined by the electrode sleeve element 195 that provides cutting electrode edge 180. The axial length C of the reduced cross-section lumen 190B can range from about 2 mm to 20 mm. In one embodiment, the first diameter A is 0.112" and the second reduced diameter B is 0.100". As shown in FIG. 5, the inner sleeve 175 can be an electrically conductive stainless steel and the reduced diameter electrode portion also can comprise a stainless steel electrode sleeve element 195 that is welded in place by weld 196 (FIG. 6A). In another alternative embodiment, the electrode and reduced diameter electrode sleeve element 195 comprises a tungsten tube that can be press fit into the distal end 198 of inner sleeve 175. FIGS. 5 and 6A further illustrates the interfacing insulation layers 202 and 204 carried by the first and second sleeves 170, 175, respectively. In FIG. 6A, the outer sleeve 170 is lined with a thin-wall insulative material 200, such as PFA, or another material described below. Similarly, the inner sleeve 175 has an exterior insulative layer 202. These coating materials can be lubricious as well as electrically insulative to reduce friction during reciprocation of the inner sleeve 175.

The insulative layers 200 and 202 described above can comprise a lubricious, hydrophobic or hydrophilic polymeric material. For example, the material can comprise a bio-compatible material such as PFA, TEFLON®, polytetrafluroethylene (PTFE), FEP (Fluorinated ethylenepropylene), polyethylene, polyamide, ECTFE (Ethylenechlorotrifluoro-ethylene), ETFE, PVDF, polyvinyl chloride or silicone.

Figure 6B:
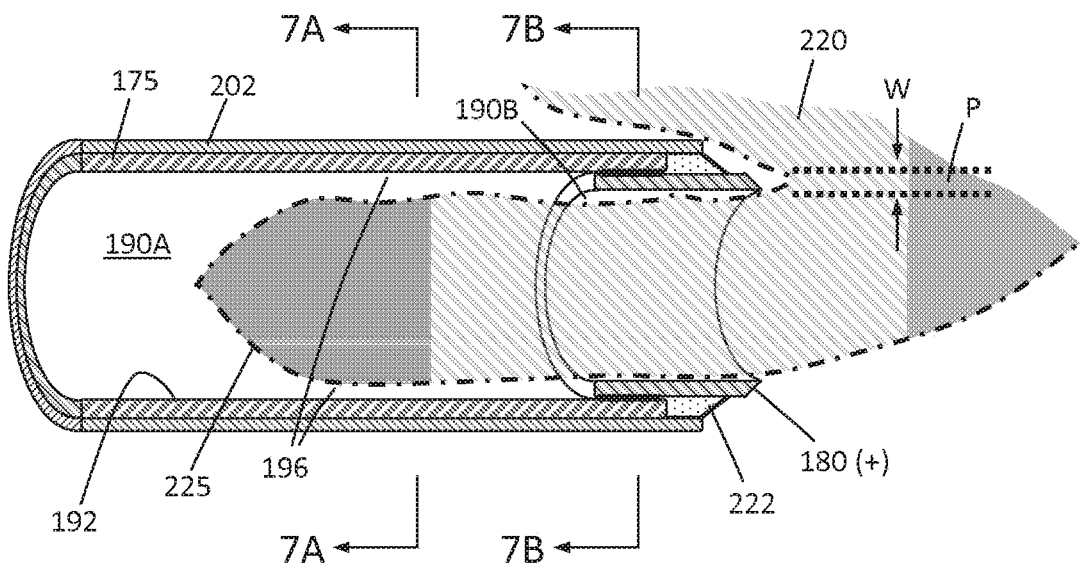
FIG. 6B is a schematic view of a distal end portion another embodiment of inner RF cutting sleeve.

Now turning to FIG. 6B, another variation of inner sleeve 175 is illustrated in a schematic view together with a tissue volume being resected with the plasma electrode edge 180. In this embodiment, as in other embodiments in this disclosure, the RF source operates at selected operational parameters to create a plasma around the electrode edge 180 of electrode sleeve 195 as is known in the art. Thus, the plasma generated at electrode edge 180 can cut and ablate a path P in the tissue 220, and is suited for cutting fibroid tissue and other abnormal uterine tissue. In FIG. 6B, the distal portion of the cutting sleeve 175 includes a ceramic collar 222 which is adjacent the distal edge 180 of the electrode sleeve 195.

The ceramic 222 collar functions to confine plasma formation about the distal electrode edge 180 and functions further to prevent plasma from contacting and damaging the polymer insulative layer 202 on the cutting sleeve 175 during operation. In one aspect of the invention, the path P cut in the tissue 220 with the plasma at electrode edge 180 provides a path P having an ablated width indicated at W, wherein such path width W is substantially wide due to tissue vaporization. This removal and vaporization of tissue in path P is substantially different than the effect of cutting similar tissue with a sharp blade edge, as in various prior art devices. A sharp blade edge can divide tissue (without cauterization) but applies mechanical force to the tissue and may prevent a large cross section slug of tissue from being cut. In contrast, the plasma at the electrode edge 180 can vaporize a path P in tissue without applying any substantial force on the tissue to thus cut larger cross sections or slugs strips of tissue. Further, the plasma cutting effect reduces the cross section of tissue strip 225 received in the tissue-extraction lumen 190B. FIG. 6B depicts a tissue strip to 225 entering lumen 190B which has such a smaller cross-section than the lumen due to the vaporization of tissue. Further, the cross section of tissue 225 as it enters the larger cross-section lumen 190A results in even greater free space 196 around the tissue strip 225. Thus, the resection of tissue with the plasma electrode edge 180, together with the lumen transition from the smaller cross-section (190B) to the larger cross-section (190A) of the tissue-extraction lumen 160 can significantly reduce or eliminate the potential for successive resected tissue strips 225 to clog the lumen. Prior art resection devices with such small diameter tissue-extraction lumen typically have problems with tissue clogging.

In another aspect of the invention, the negative pressure source 225 coupled to the proximal end of tissue-extraction lumen 160 (see FIGS. 1 and 4) also assists in aspirating and moving tissue strips 225 in the proximal direction to a collection reservoir (not shown) outside the handle 142 of the device.

Figure 7A:
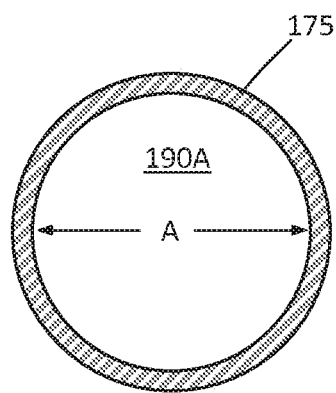
FIG. 7A is a cross sectional view of the inner RF cutting sleeve of FIG. 6B taken along line 7A-7A of FIG. 6B.
Figure 7B:
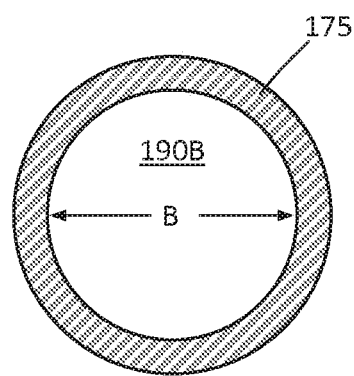
FIG. 7B is another cross sectional view of the inner RF cutting sleeve of FIG. 6B taken along line 7B-7B of FIG. 6B.
Figure 8:
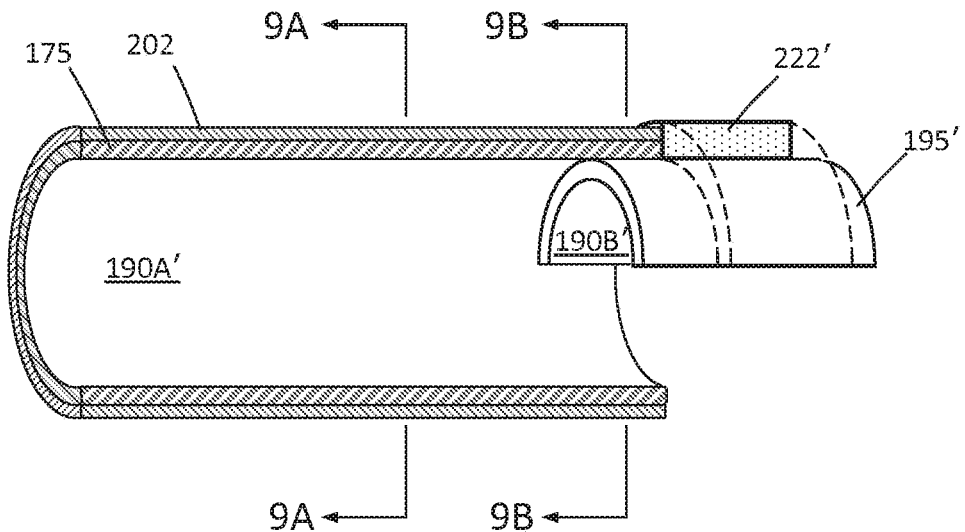
FIG. 8 is a schematic view of a distal end portion of another embodiment of inner RF cutting sleeve.
Figure 9A:
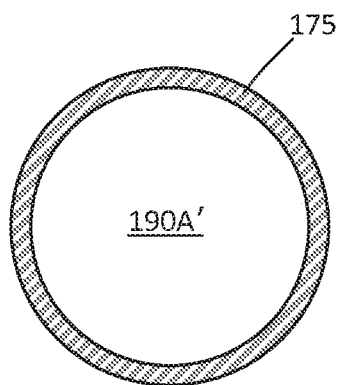
FIG. 9A is a cross sectional view of the RF cutting sleeve of FIG. 8 taken along line 9A-9A of FIG. 8.
Figure 9B:
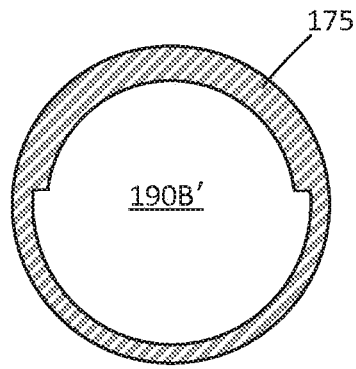
FIG. 9B is a cross sectional view of the RF cutting sleeve of FIG. 8 taken along line 9B-9B of FIG. 8.

FIGS. 7A-7B illustrate the change in lumen diameter of cutting sleeve 175 of FIG. 6B. FIG. 8 illustrates the distal end of a variation of cutting sleeve 175' which is configured with an electrode cutting element 195' that is partially tubular in contrast to the previously described tubular electrode element 195 (FIGS. 5 and 6A). FIGS. 9A-9B again illustrate the change in cross-section of the tissue-extraction lumen between reduced cross-section region 190B' and the increased cross-section region 190A' of the cutting sleeve 175' of FIG. 8. Thus, the functionality remains the same whether the cutting electrode element 195' is tubular or partly tubular. In FIG. 8A, the ceramic collar 222' is shown, in one variation, as extending only partially around sleeve 175 to cooperate with the radial angle of cutting electrode element 195'. Further, the variation of FIG. 8 illustrates that the ceramic collar 222' has a larger outside diameter than insulative layer 202. Thus, friction may be reduced since the short axial length of the ceramic collar 222' interfaces and slides against the interfacing insulative layer 200 about the inner surface of lumen 172 of outer sleeve 170.

In general, one aspect of the invention comprises a tissue cutting and extracting device (FIGS. 10A-11C) that includes first and second concentric sleeves having an axis and wherein the second (inner) sleeve 175 has an axially-extending tissue-extraction lumen therein, and wherein the second sleeve 175 is moveable between axially non-extended and extended positions relative to a tissue-receiving window 176 in first sleeve 170 to resect tissue, and wherein the tissue extraction lumen 160 has first and second cross-sections. The second sleeve 175 has a distal end configured as a plasma electrode edge 180 to resect tissue disposed in tissue-receiving window 176 of the first sleeve 170. Further, the distal end of the second sleeve, and more particularly, the electrode edge 180 is configured for plasma ablation of a substantially wide path in the tissue. In general, the tissue-extraction device is configured with a tissue extraction lumen 160 having a distal end portion with a reduced cross-section that is smaller than a cross-section of medial and proximal portions of the lumen 160.

In one aspect of the invention, referring to FIGS. 7A-7B and 9A-9B, the tissue-extraction lumen 160 has a reduced cross-sectional area in lumen region 190A proximate the plasma cutting tip or electrode edge 180 wherein said reduced cross section is less that 95%, 90%, 85% or 80% than the cross sectional area of medial and proximal portions 190B of the tissue-extraction lumen, and wherein the axial length of the tissue-extraction lumen is at least 10 cm, 20 cm, 30 cm or 40 cm. In one embodiment of tissue-cutting device 100 for hysteroscopic fibroid cutting and extraction (FIG. 1), the shaft assembly 140 of the tissue-cutting device is 35 cm in length.

Figure 10A:
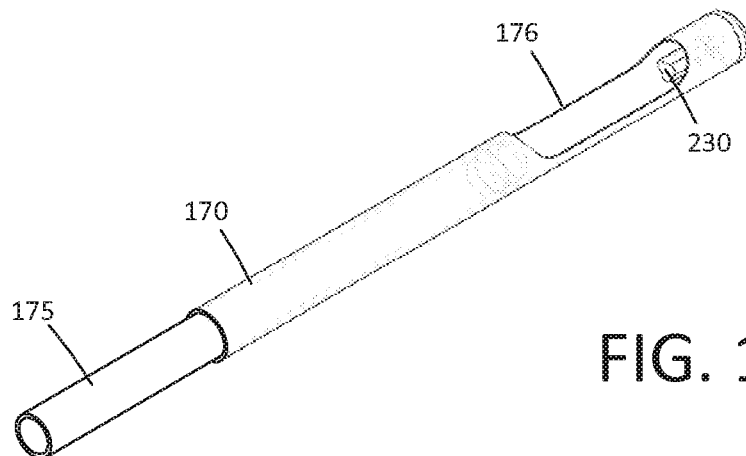
FIG. 10A is a perspective view of the working end of the tissue-cutting device of FIG. 1 with the reciprocating RF cutting sleeve in a non-extended position.
Figure 10B:
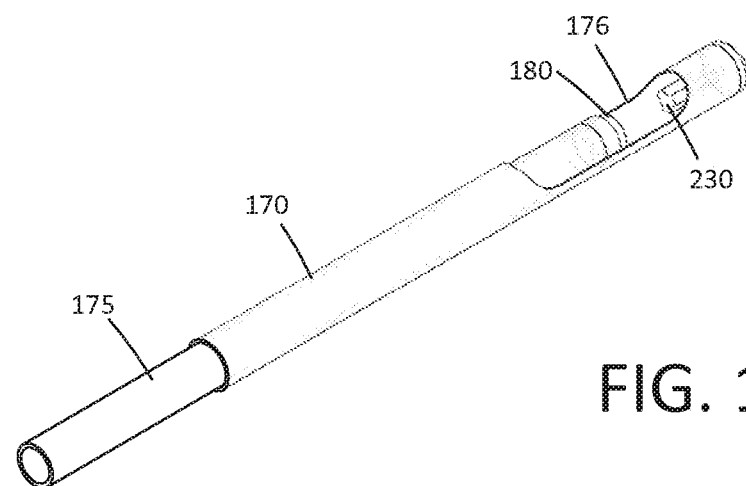
FIG. 10B is a perspective view of the tissue-cutting device of FIG. 1 with the reciprocating RF cutting sleeve in a partially extended position.
Figure 10C:
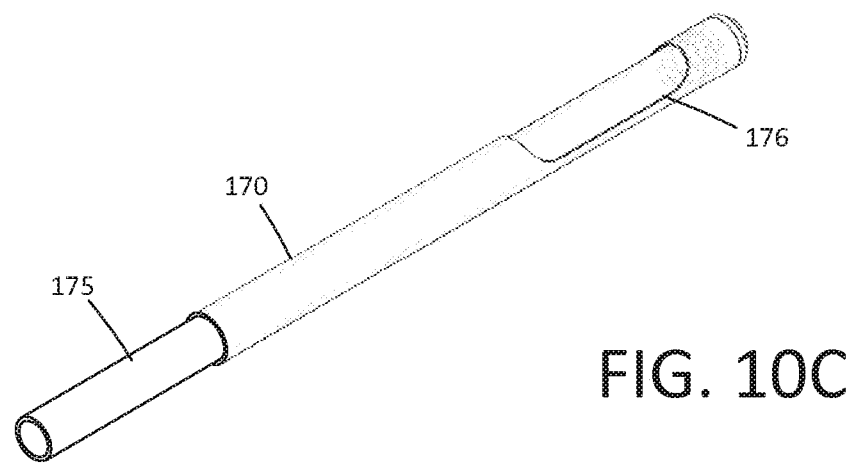
FIG. 10C is a perspective view of the tissue-cutting device of FIG. 1 with the reciprocating RF cutting sleeve in a fully extended position across the tissue-receiving window.
Figure 11A:
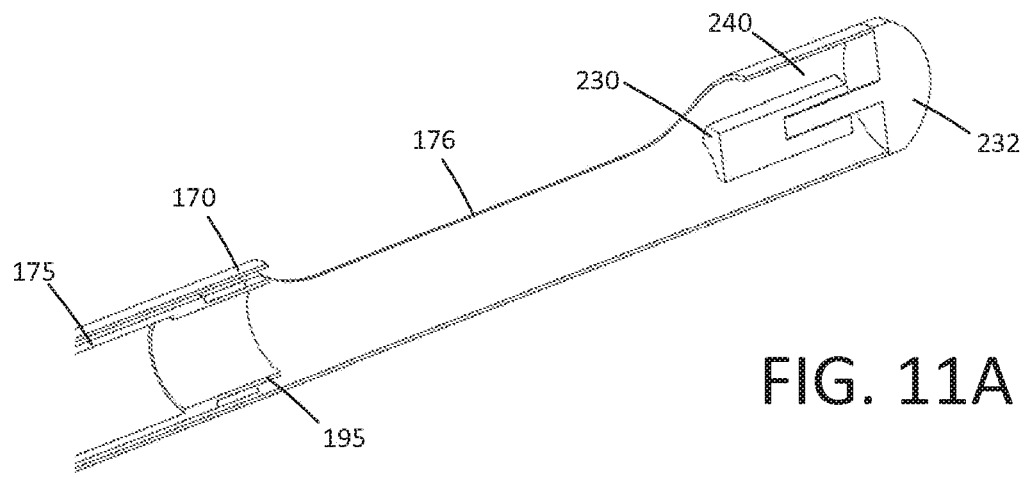
FIG. 11A is a sectional view of the working end of the tissue-cutting device of FIG. 10A with the reciprocating RF cutting sleeve in a non-extended position.
Figure 11B:
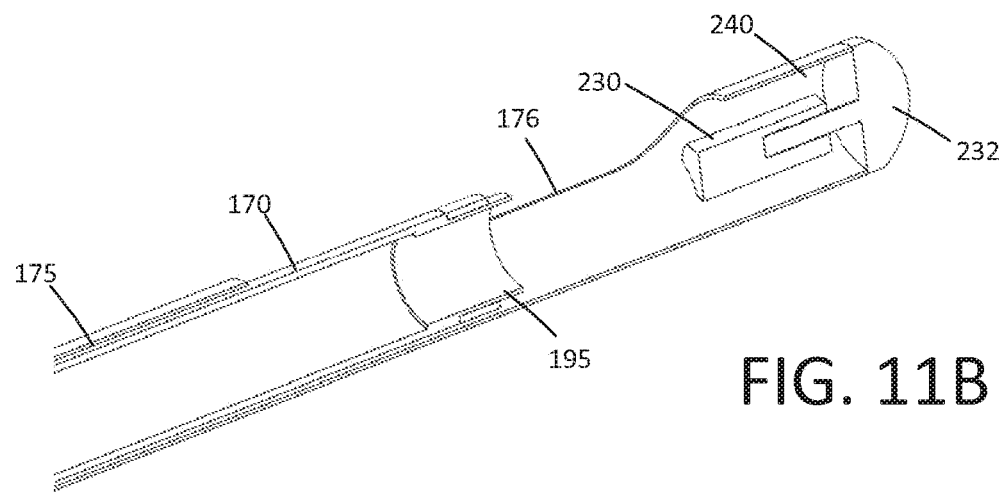
FIG. 11B is a sectional view of the working end of FIG. 10B with the reciprocating RF cutting sleeve in a partially extended position.
Figure 11C:
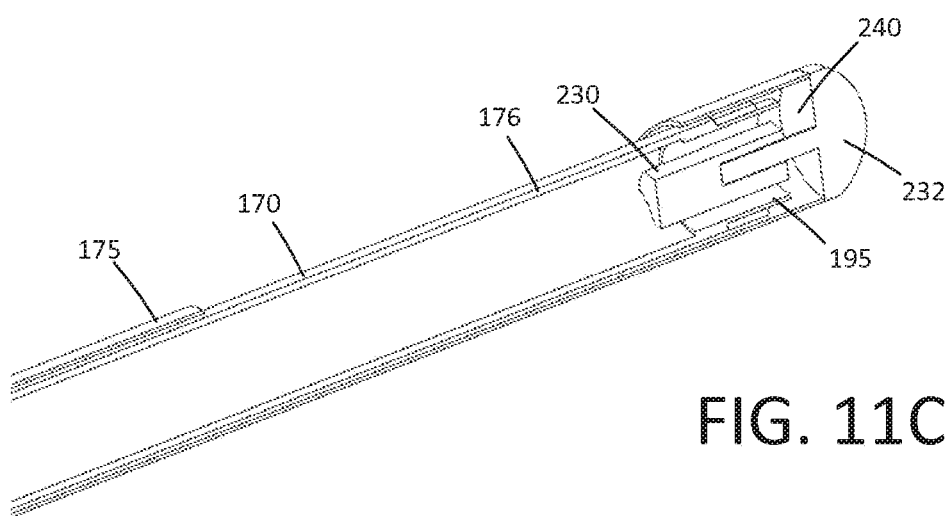
FIG. 11C is a sectional view of the working end of FIG. 10C with the reciprocating RF cutting sleeve in a fully extended position.

FIGS. 10A-10C illustrate the working end 145 of the tissue-cutting device 100 with the reciprocating cutting sleeve or inner sleeve 175 in three different axial positions relative to the tissue receiving window 176 in outer sleeve 170. In FIG. 10A, the cutting sleeve 175 is shown in a retracted or non-extended position in which the sleeve 175 is at it proximal limit of motion and is prepared to advance distally to an extended position to thereby electrosurgically cut tissue positioned in and/or suctioned into in window 176. FIG. 10B shows the cutting sleeve 175 moved and advanced distally to a partially advanced or medial position relative to tissue cutting window 176. FIG. 10C illustrates the cutting sleeve 175 fully advanced and extended to the distal limit of its motion wherein the plasma cutting electrode 180 has extended past the distal end 226 of tissue-receiving window 176 at which moment the resected tissue strip 225 in excised from tissue volume 220 and captured in reduced cross-sectional lumen region 190A.

Now referring to FIGS. 10A-10C and FIGS. 11A-11C, another aspect of the invention comprises "tissue displacement" mechanisms provided by multiple elements and processes to "displace" and move tissue strips 225 in the proximal direction in lumen 160 of cutting sleeve 175 to thus ensure that tissue does not clog the lumen of the inner sleeve 175. As can be seen in FIG. 10A and the enlarged views of FIGS. 11A-11C, one tissue displacement mechanism comprises a projecting element 230 that extends proximally from distal tip 232 which is fixedly attached to outer sleeve 170. The projecting element 230 extends proximally along central axis 168 in a distal chamber 240 defined by outer sleeve 170 and distal tip 232. In one embodiment depicted in FIG. 11A, the shaft-like projecting element 230, in a first functional aspect, comprises a mechanical pusher that functions to push a captured tissue strip 225 proximally from the small cross-section lumen 190B of cutting sleeve 175 as the cutting sleeve 175 moves to its fully advanced or extended position. In a second functional aspect, the chamber 240 in the distal end of sleeve 170 is configured to capture a volume of saline distending fluid 244 from the working space, and wherein the existing RF electrodes of the working end 145 are further configured to explosively vaporize the captured fluid 244 to generate proximally-directed forces on tissue strips 225 resected and disposed in lumen 160 of the cutting sleeve 175. Both of these two functional elements and processes (tissue displacement mechanisms) can apply a substantial mechanical force on the captured tissue strips 225 by means of the explosive vaporization of liquid in chamber 240 and can function to move tissue strips 225 in the proximal direction in the tissue-extraction lumen 160. It has been found that using the combination of multiple functional elements and processes can virtually eliminate the potential for tissue clogging the tissue extraction lumen 160.

Figure 12A:
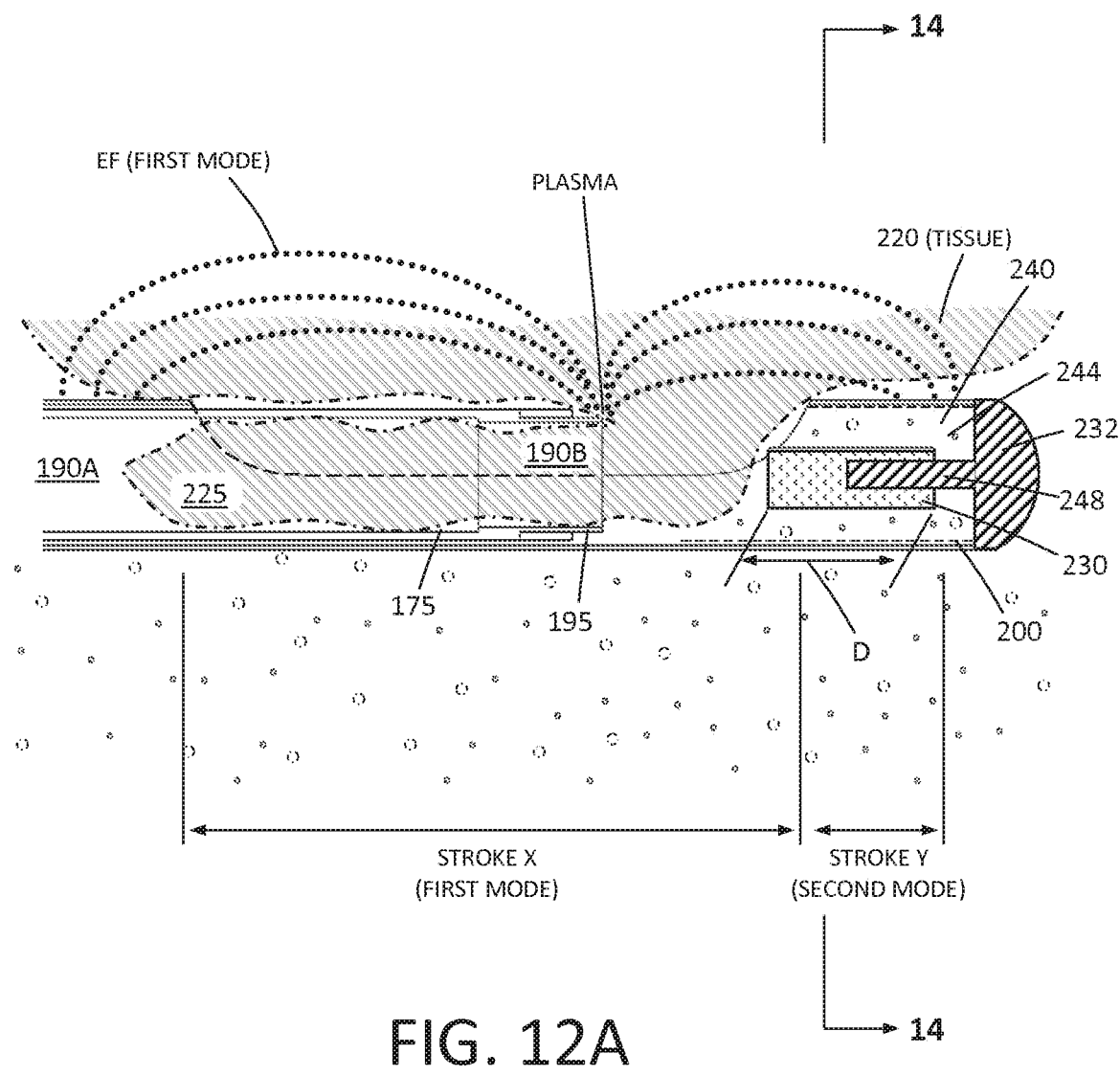
FIG. 12A is an enlarged sectional view of the working end of tissue-cutting device of FIG. 11B with the reciprocating RF cutting sleeve in a partially extended position showing the RF field in a first RF mode and plasma cutting of tissue.
Figure 12B:
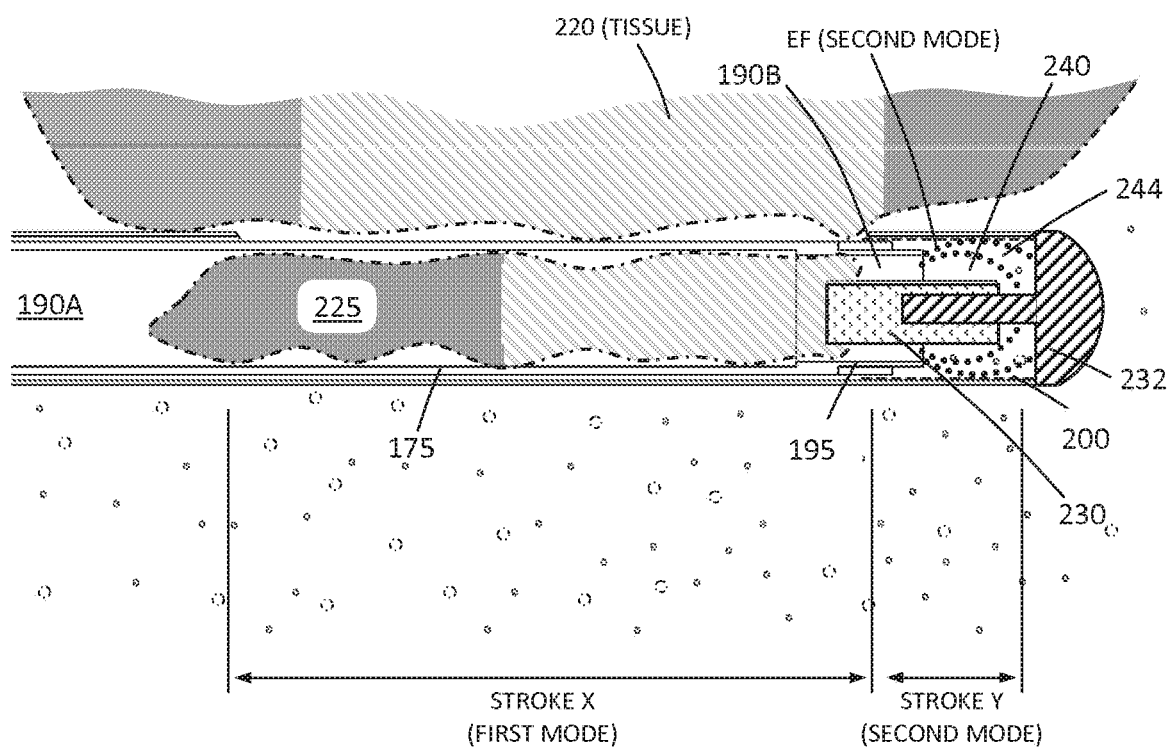
FIG. 12B is an enlarged sectional view of the working end of FIG. 11C with the reciprocating RF cutting sleeve almost fully extended and showing the RF fields switching to a second RF mode from a first RF mode shown in FIG. 12.
Figure 12C:
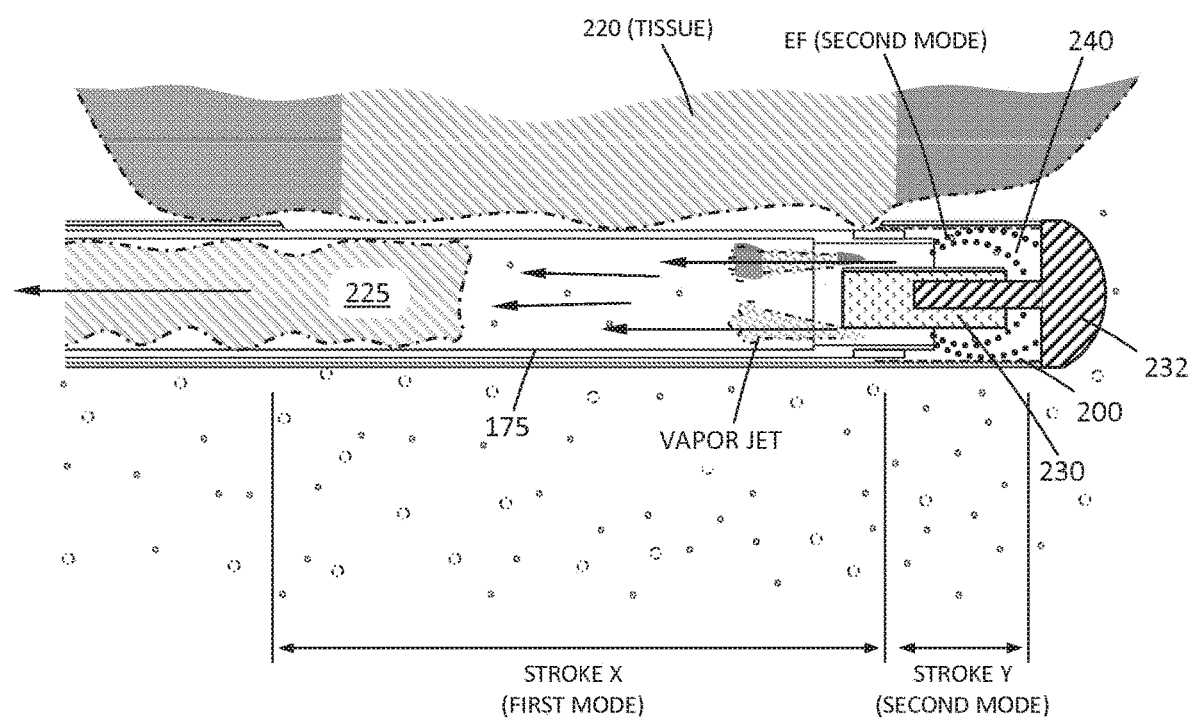
FIG. 12C is an enlarged sectional view of the working end of FIG. 11C with the reciprocating RF cutting sleeve again almost fully extended and showing the explosive vaporization of a captured liquid volume to expel cut tissue in the proximal direction.

More in particular, FIGS. 12A-12C illustrate sequentially the functional aspects of the tissue displacement mechanisms and the explosive vaporization of fluid captured in chamber 240. In FIG. 12A, the reciprocating cutting sleeve 175 is shown in a medial position advancing distally wherein plasma at the cutting electrode edge 180 is cutting a tissue strip 225 that is disposed within lumen 160 of the cutting sleeve 175. In FIG. 12A-12C, it can be seen that the system operates in first and second electrosurgical modes corresponding to the reciprocation and axial range of motion of cutting sleeve 175 relative to the tissue-receiving window 176. As used herein, the term "electrosurgical mode" refers to which electrode of the two opposing polarity electrodes functions as an "active electrode" and which electrode functions as a "return electrode". The terms "active electrode" and "return electrode" are used in accordance with convention in the art—wherein an active electrode has a smaller surface area than the return electrode which thus focuses RF energy density about such an active electrode. In the working end 145 of FIGS. 10A-11C, the cutting electrode element 195 and its cutting electrode edge 180 must comprise the active electrode to focus energy about the electrode to generate the plasma for tissue cutting. Such a high-intensity, energetic plasma at the electrode edge 180 is needed throughout stroke X indicated in FIG. 12A-12B to cut tissue. The first mode occurs over an axial length of travel of inner cutting sleeve 175 as it crosses the tissue-receiving window 176, at which time the entire exterior surface of outer sleeve 170 comprises the return electrode indicated at 185. The electrical fields EF of the first RF mode are indicated generally in FIG. 12A.

Figure 14:
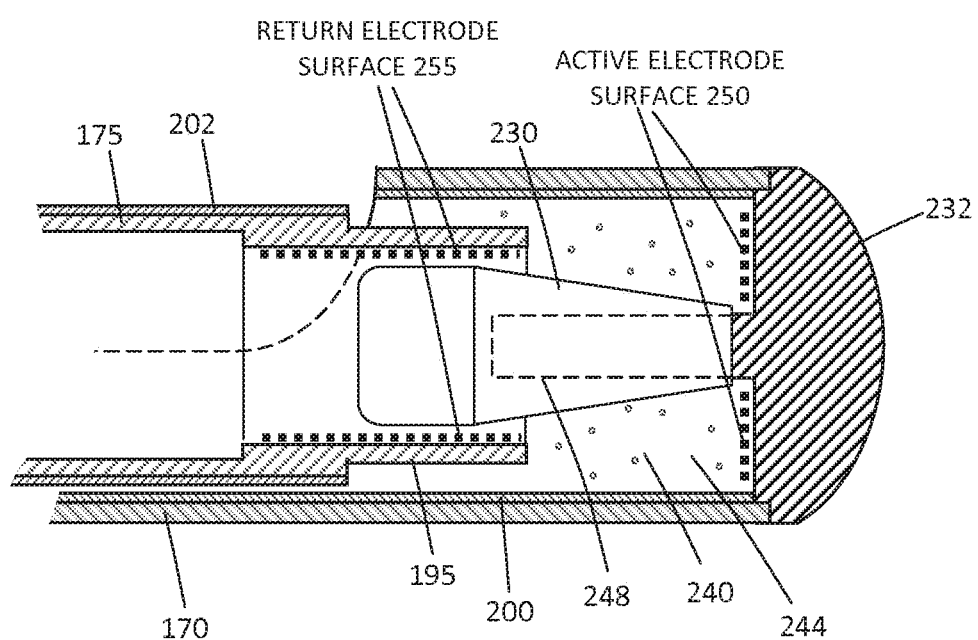
FIG. 14 is a sectional view of the working end of FIG. 12C showing an interior chamber and a variation of a projecting element.

FIG. 12B illustrates the moment in time at which the distal advancement or extension of inner cutting sleeve 175 entirely crossed the tissue-receiving window 176. At this time, the electrode sleeve 195 and its electrode edge 180 are confined within the mostly insulated-wall chamber 240 defined by the outer sleeve 170 and distal tip 232. At this moment, the system is configured to switch to the second RF mode in which the electric fields EF switch from those described previously in the first RF mode. As can be seen in FIG. 12B, in this second mode, the limited interior surface area 250 of distal tip 232 that interfaces chamber 240 functions as an active electrode and the distal end portion of cutting sleeve 175 exposed to chamber 240 acts as a return electrode. In this mode, very high energy densities occur about surface 250 and such a contained electric field EF can explosively and instantly vaporize the fluid 244 captured in chamber 240. The expansion of water vapor can be dramatic and can thus apply tremendous mechanical forces and fluid pressure on the tissue strip 225 to move the tissue strip in the proximal direction in the tissue extraction lumen 160. FIG. 12C illustrates such explosive or expansive vaporization of the distention fluid 244 captured in chamber 240 and further shows the tissue strip 225 being expelled in the proximal direction the lumen 160 of inner cutting sleeve 175. FIG. 14 further shows the relative surface areas of the active and return electrodes at the extended range of motion of the cutting sleeve 175, again illustrating that the surface area of the non-insulated distal end surface 250 is small compared to surface 255 of electrode sleeve which comprises the return electrode.

Still referring to FIGS. 12A-12C, it has been found that a single power setting on the RF source 150 and controller 155 can be configured both (i) to create plasma at the electrode cutting edge 180 of electrode sleeve 195 to cut tissue in the first mode, and (ii) to explosively vaporize the captured distention fluid 244 in the second mode. Further, it has been found that the system can function with RF mode-switching automatically at suitable reciprocation rates ranging from 0.5 cycles per second to 8 or 10 cycles per second. In bench testing, it has been found that the tissue-cutting device described above can cut and extract tissue at the rate of from 4 grams/min to 8 grams/min without any potential for tissue strips 225 clogging the tissue-extraction lumen 160. In these embodiments, the negative pressure source 125 also is coupled to the tissue-extraction lumen 160 to assist in applying forces for tissue extraction.

Of particular interest, the fluid-capture chamber 240 defined by sleeve 170 and distal tip 232 can be designed to have a selected volume, exposed electrode surface area, length and geometry to optimize the application of expelling forces to resected tissue strips 225. In one embodiment, the diameter of the chamber is 3.175 mm and the length is 5.0 mm which taking into account the projecting element 230, provided a captured fluid volume of approximately 0.040 mL. In other variations, the captured fluid volume can range from 0.004 to 0.080 mL.

In one example, a chamber 240 with a captured liquid volume of 0.040 mL together with 100% conversion efficiency in and instantaneous vaporization would require 103 Joules to heat the liquid from room temperature to water vapor. In operation, since a Joule is a W*s, and the system reciprocate at 3 Hz, the power required would be on the order of 311 W for full, instantaneous conversion to water vapor. A corresponding theoretical expansion of 1700× would occur in the phase transition, which would results in up to 25,000 psi instantaneously (14.7 psi×1700), although due to losses in efficiency and non-instantaneous expansion, the actual pressures would be much less. In any event, the pressures are substantial and can apply significant expelling forces to the captured tissue strips 225.

Figure 13:
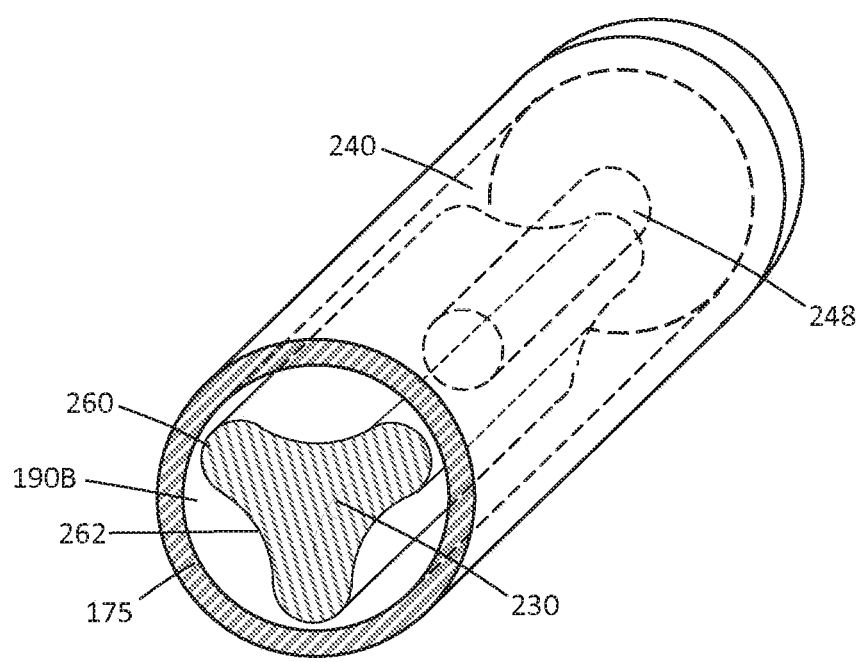
FIG. 13 is an enlarged perspective view of a portion of the working end of FIG. 12C showing an interior chamber and a fluted projecting element.

Referring to FIG. 12A, the interior chamber 240 can have an axial length from about 0.5 mm to 10 mm to capture a liquid volume ranging from about 0.004 mL 0.01 mL. It can be understood in FIG. 12A, that the interior wall of chamber 240 has an insulator layer 200 which thus limits the electrode surface area 250 exposed to chamber 240. In one embodiment, the distal tip 232 is stainless steel and is welded to outer sleeve 170. The post element 248 is welded to tip 232 or machined as a feature thereof. The projecting element 230 in this embodiment is a non-conductive ceramic. FIG. 13 shows the cross-section of the ceramic projecting element 230 which is fluted, which in one embodiment has three flute elements 260 in three corresponding axial grooves 262 in its surface. Any number of flutes, channels or the like is possible, for example from 2 to about 20. The purpose of this design is to provide a significant cross-sectional area at the proximal end of the projecting element 230 to push the tissue strip 225, while at the same time the three grooves 262 permit the proximally-directed jetting of water vapor to impact the tissue exposed to the grooves 262. In one embodiment, the axial length D of the projecting element 230 is configured to push tissue entirely out of the reduced cross-sectional region 190B of the electrode sleeve element 195. In another embodiment, the volume of the chamber 240 is configured to capture liquid that when explosively vaporized provided a gas (water vapor) volume sufficient to expand into and occupy at least the volume defined by a 10% of the total length of extraction channel 160 in the device, at least 20% of the extraction channel 160, at least 40% of the extraction channel 160, at least 60% of the extraction channel 160, at least 80% of the extraction channel 160 or at least 100% of the extraction channel 160.

As can be understood from FIGS. 12A to 12C, the distending fluid 244 in the working space replenishes the captured fluid in chamber 240 as the cutting sleeve 175 moves in the proximal direction or towards its non-extended position. Thus, when the cutting sleeve 175 again moves in the distal direction to cut tissue, the interior chamber 240 is filled with fluid 244 which is then again contained and is then available for explosive vaporization as described above when the cutting sleeve 175 closes the tissue-receiving window 176. In another embodiment, a one-way valve can be provided in the distal tip 232 to draw fluid directly into interior chamber 240 without the need for fluid to migrate through window 176.

Figure 15:
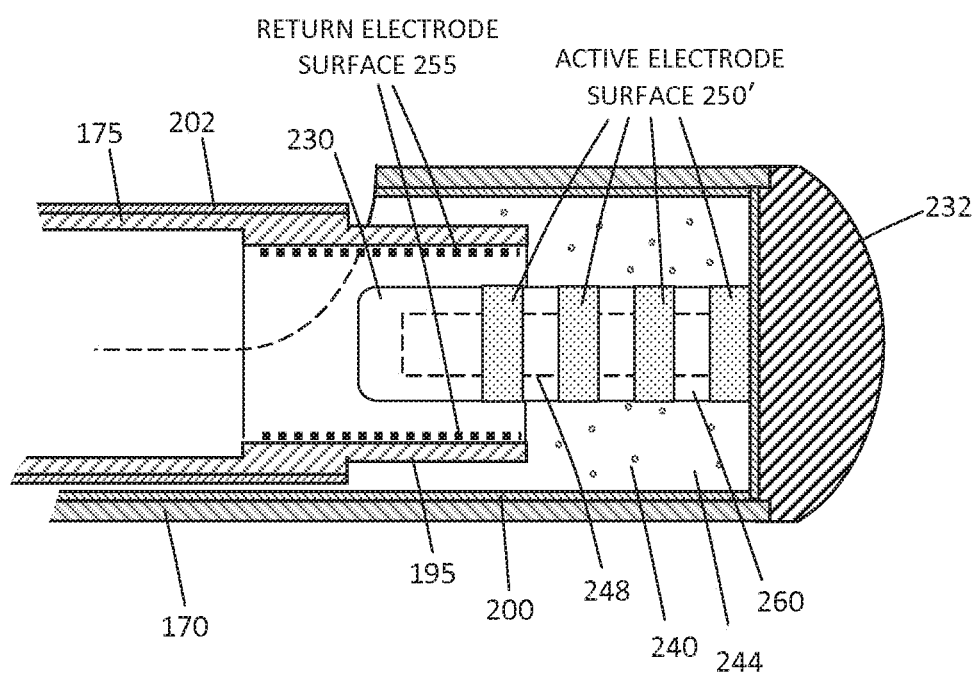
FIG. 15 is a sectional view of the working end of FIG. 12C showing an interior chamber and a variation of a projecting element configured to explosively vaporize the captured liquid volume.

FIG. 15 illustrates another variation in which the active electrode surface area 250' in the second mode comprises a projecting element 230 with conductive regions and non-conductive regions 260 which can have the effect of distributing the focused RF energy delivery over a plurality of discrete regions each in contact with the captured fluid 244. This configuration can more efficiently vaporize the captured fluid volume in chamber 240. In one embodiment, the conductive regions 250' can comprise metal discs or washers on post 248. In other variation (not shown) the conductive regions 250' can comprise holes, ports or pores in a ceramic material 260 fixed over an electrically conductive post 248.

In another embodiment, the RF source 150 and controller 155 can be programmed to modulate energy delivery parameters during stroke X and stroke Y in FIGS. 12A-12C to provide the optimal energy (i) for plasma cutting with electrode edge 180, and (ii) for explosively vaporizing the captured fluid in chamber 240.

Figure 16A:
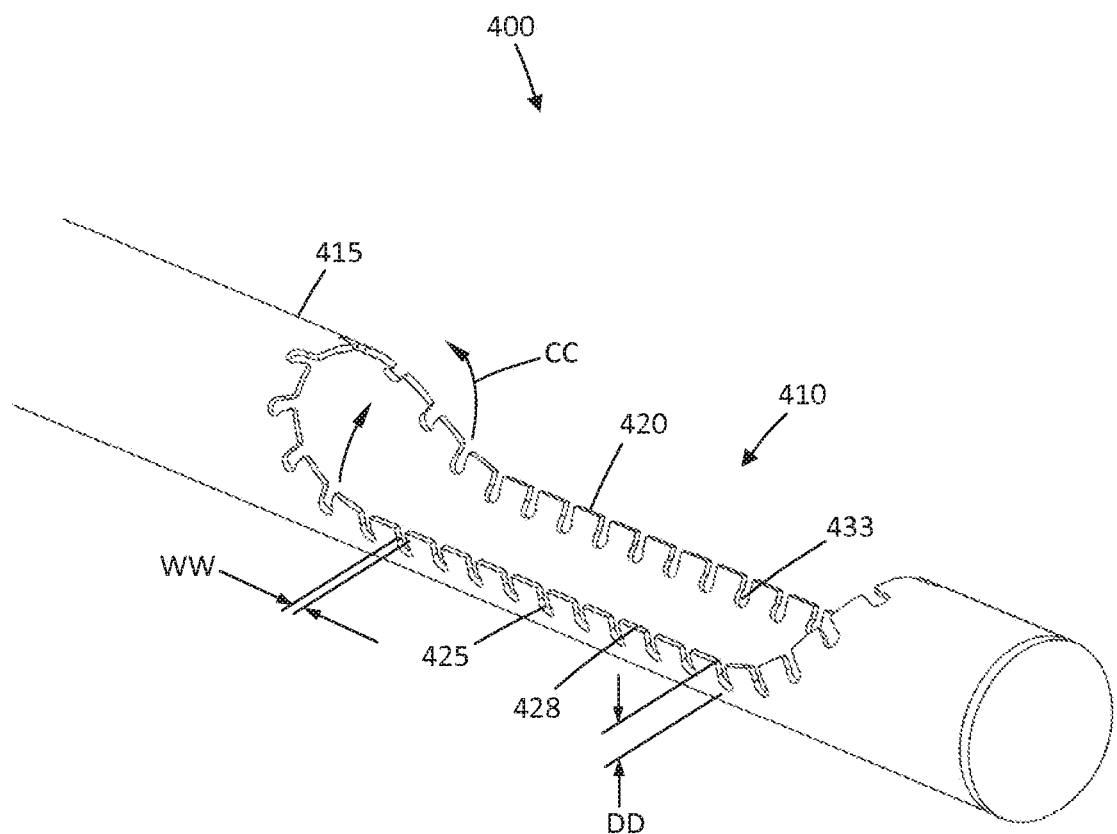
FIG. 16A is a view of the working end of an outer sleeve with window having edge features prepared for coupling with a dielectric material.
Figure 16B:
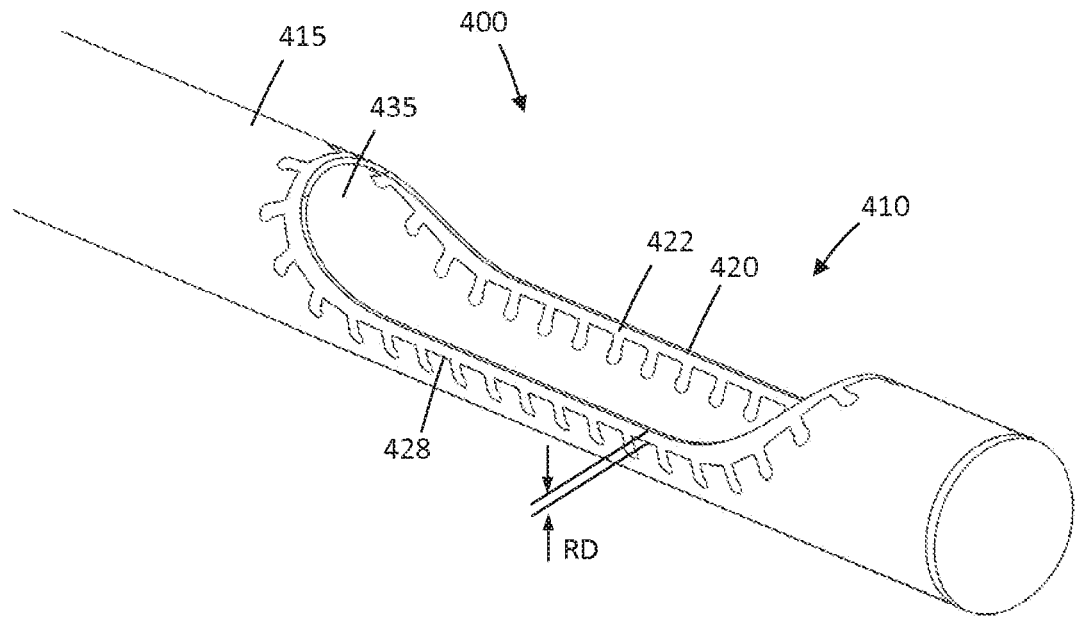
FIG. 16B is a view of the working end of the outer sleeve of FIG. 16A after coupling with the dielectric edge.
Figure 16C:
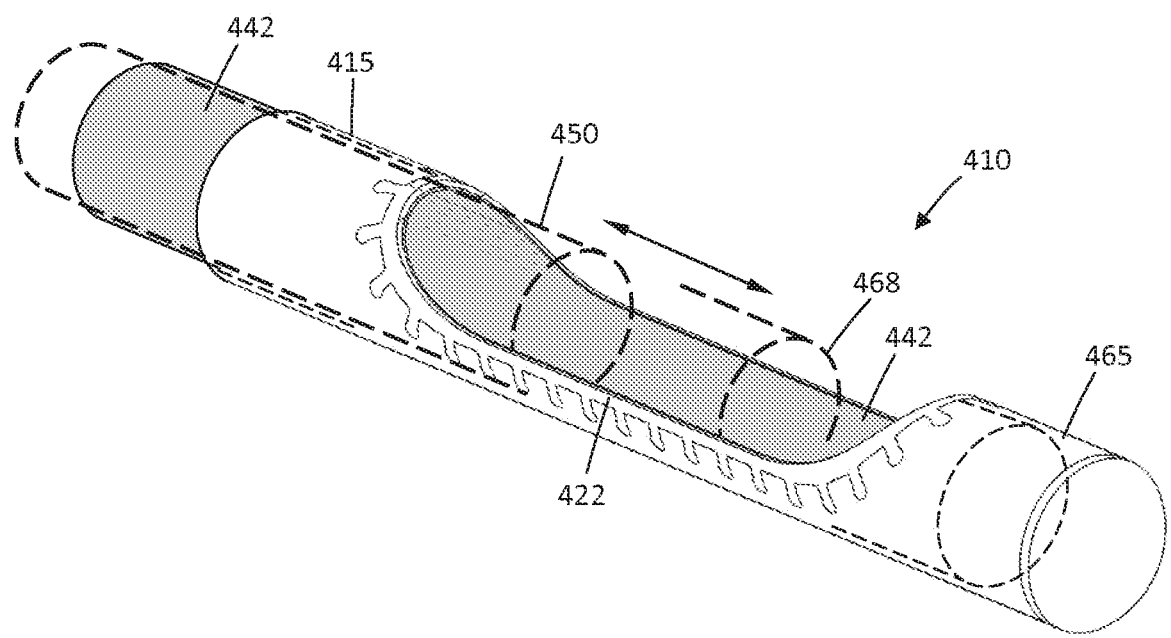
FIG. 16C is another view of the working end of the outer sleeve of FIG. 16A after coupling an additional dielectric inner sleeve material.
Figure 17:
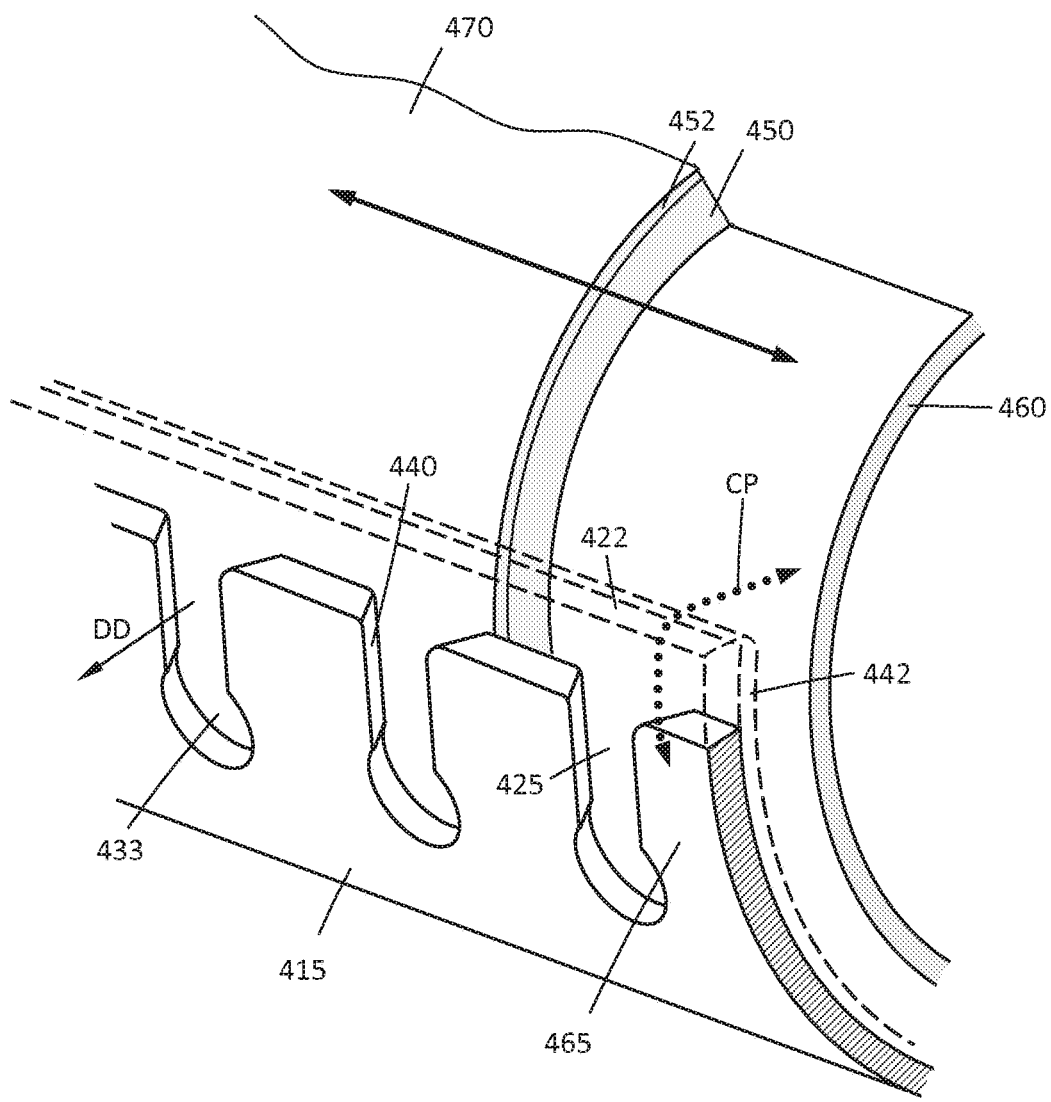
FIG. 17 is an enlarged view of a portion of a working end as in FIGS. 16A-16C showing dielectric m

FIGS. 16A-16 and FIG. 17 illustrate another embodiment RF cutting probe 400 that is similar to the above described embodiments. The variation of FIGS. 16A-16C includes dielectric features and components in the working end that permit optimal generation of plasma about the RF cutting electrode carried by the inner cutting sleeve.

FIGS. 16A-16B illustrate the working end of probe 400 and more particularly distal end 410 of the outer cutting sleeve 415 and the window 420 therein. This embodiment, in its final assembly shown in FIG. 16B, provides a dielectric window edge 422 that comprises a dielectric material of a similar thickness as the wall thickness of the outer sleeve 415. This wall thickness can range from about 0.003" to 0.010". As can be seen in FIG. 16B, the window 420 in outer cutting sleeve 415 is configured with a plurality of "key" features 425 that permit secure coupling of the dielectric edge 422 to the sleeve 415.

FIG. 16A illustrates the metal outer sleeve 415 as manufactured without integration of the dielectric edge 422. It can be seen that a plurality of keys 425 are machined into the metal window edge or interface 428, wherein the term keys is used to mean features that greatly increase the surface area of the window edge perimeter or interface 428 that interfaces with a molded-in dielectric material 422. In one embodiment, the metal window edge 428 has cut features or keys 425 that have a width WW ranging from 0.002" to 0.020" and a depth DD of 0.002" to 0.020". In one aspect of the invention, the surface area of the edge interface 428 is at least 200%, 300%, 400% or 500% greater than a window edge without such keys 425. In one variation in FIGS. 16A and 17, it can be seen that each key 425 is configured with an increased cross section feature 433 which will resist de-coupling forces in the rotational direction indicated arrow CC in FIG. 16A. In the enlarged view of FIG. 17, another variation includes radially slanted or beveled edges 440 on keys 425 to further resist de-coupling forces in an outward direction indicated at arrow DD.

Now turning to FIG. 16B, a method of making the distal end 410 can be understood. In a method of manufacturing, the dielectric polymer material 422 is molded in place as depicted in FIG. 16B by inserting a core pin in the lumen 435 the keyed outer sleeve 415 as shown in FIG. 16A. The core pin matches the diameter of lumen 435 in the outer sleeve 415. Thereafter, an outer mold component (not shown) is placed around the exterior of outer sleeve 415 with the mold component matching the O.D. of the outer sleeve 415. Thereafter, a polymer can be injected into the space between the core pin and outer mold which is equivalent to the sleeve wall in the space left by the window 420. In an injection molding process, polymer can be injected to infill the keys 425 in the outer sleeve 415 as well as the window 420. Thereafter, the final window 420 can be cut out leaving the dielectric edge 422 having a suitable radial dimension RD around the window which can range from about 0.005" to 0.025" as depicted in FIG. 16B. In one embodiment, the dielectric material can be ABS, Nylon or polypropylene. In one variation, the dielectric material has a comparative tracking index value ranging from 200 volts to 800 volts which helps to insure that the dielectric material remains intact throughout a tissue cutting procedure. In other variations, the dielectric material can comprise at least one of a polymer, ceramic, or glass.

It can be understood from FIG. 16A that the keys 425 of sleeve 415 will lock the dielectric edge 422 in place to prevent rotational or axial movement of the dielectric edge 422 relative to the sleeve 415. Now turning to FIG. 17, it should be appreciated keys 425 can be further shaped to prevent radial outward displacement of the dielectric edge 422 relative to the metal sleeve 415. In the enlarged view of FIG. 17, this variation includes radially slanted or beveled edges 440 on keys 425 to further resist de-coupling forces in an outward direction indicated at arrow DD.

FIG. 16C illustrates a final step in assembling an outer sleeve 415 which comprises bonding a thin wall dielectric material or layer 442 in the lumen 435 of the outer sleeve. This dielectric material 442 can be any suitable polymer, such as FEP, Teflon, etc., and can have a thickness ranging from about 0.001" to 0.010" and functions to separate the conductive inner sleeve 450 from the conductive outer sleeve 415 which comprise opposing polarity electrodes as described in previous embodiments. FIG. 17 shows that the dielectric layer 442 overlaps and is bonded to the dielectric edge 422 shown in phantom view. The inner dielectric layer 442 lining the outer sleeve 415 has a further function in that it provides a lubricious surface against which the inner sleeve 450 can reciprocate. In another variation shown in FIG. 17, the inner sleeve 450 can be fabricated with an outer polymer dielectric layer 452 which serves a further electrical insulation and as a lubricious layer between the sleeves 415 and 450.

FIG. 16C further shows the inner cutting sleeve 450 in phantom view disposed within the lumen 435 of the outer sleeve 415 in its reciprocating stroke. In one aspect of the invention, the dielectric edge 422 of the window 420 is configured to provide a predetermined dimensional range between the first polarity RF cutting electrode 460 (see FIG. 17) and the exposed surface 465 of outer sleeve 415 which comprises the second polarity electrode. In FIG. 16C, the distal end 468 of the inner cutting sleeve 450 is shown in phantom view in two axial positions in the window 420. It should be appreciated that the stroke of the inner cutting sleeve 450 extends over the length of the window which can range from about 5 mm to 25 mm or more. The configuration the dielectric edge 422 and the dielectric layer 442 in that the first polarity electrode 460 carried by inner sleeve 450 and a second polarity electrode 465 (comprising an exterior surface of outer sleeve 425) is maintained in a very narrow dimensional range no matter the location of inner sleeve 450 in its stroke. In one aspect the invention, the working end assembly in configured to maintain spacing between the first and second polarity electrodes, or stated differently, to maintain the length of the RF current path CP (see FIG. 17) throughout the stroke between 0.015" and 0.050".

More specifically, referring to FIG. 17, the dimension of the current path CP between the RF cutting electrode 460 and the electrode surface 465 of outer sleeve 415 about the window 420 is shown. In FIG. 17, it can be seen that the cutting electrode 460, as described in previous embodiments, is stepped down in diameter from larger diameter portion 470 of inner sleeve 450 that slidably contacts the lumen 435 in outer sleeve 415. As described above in relation to FIGS. 8 and 9, the step down in diameter of the RF cutting electrode sleeve can range from 0.010" to 0.040". Further, in the embodiment shown in FIG. 17, the inner sleeve 450 is shown configured with optional dielectric exterior layer 452 with a thickness of 0.001" to 0.010" that slidably cooperates with dielectric lining 442 of the outer sleeve. In FIG. 17, the shortest dimension of the current path CP between the opposing polarity electrodes thus consists of current path portion radially outward from the RF electrode 460 over the dielectric edge 422 and then circumferentially downward in current path portion to the metal electrode 465 about the keys 425. It has been found by maintaining the precise spacing between the opposing polarity electrodes throughout the stroke of the inner sleeve 450 can optimize plasma formation at the distal edge of the RF cutting electrode 460 for cutting tissue.

In another aspect of the invention, referring to FIG. 17, the minimum cross-sectional area of the tissue-extracting channel in the inner sleeve 450 is at least 40%, at least 45% or at least 50% of the cross-sectional area of outer sleeve 415. The relation between cross sections or components of the inner sleeve 450 and outer sleeve provides another manner in which the spacing of opposing polarity electrodes can be stated since each or the sleeves functions as a different polarity electrode.

Figure 18:
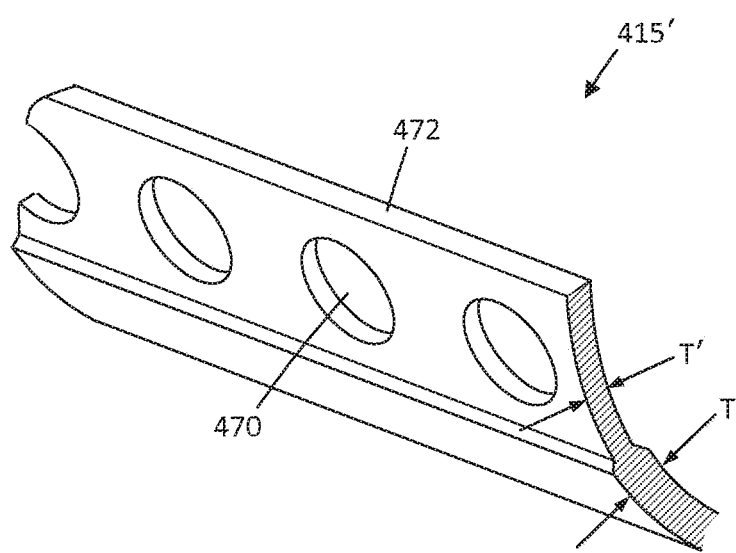
FIG. 18 is a view of another working end of an outer sleeve different edge features prepared for coupling with a dielectric material.

FIG. 18 illustrates another embodiment of outer sleeve 415' in which the keys take an alternative form. In FIG. 18, the keys comprise a plurality of windows 470 through which polymer dielectric edge 422 can be injection molded. Further, the wall of outer sleeve 415' at the window perimeter 472 can be reduced in cross-section from wall thickness T to lesser thickness T'. As can be understood from FIG. 18, the dielectric edge 422 when over-molded then can match the thickness of the wall of outer sleeve 415'.

Figure 19:
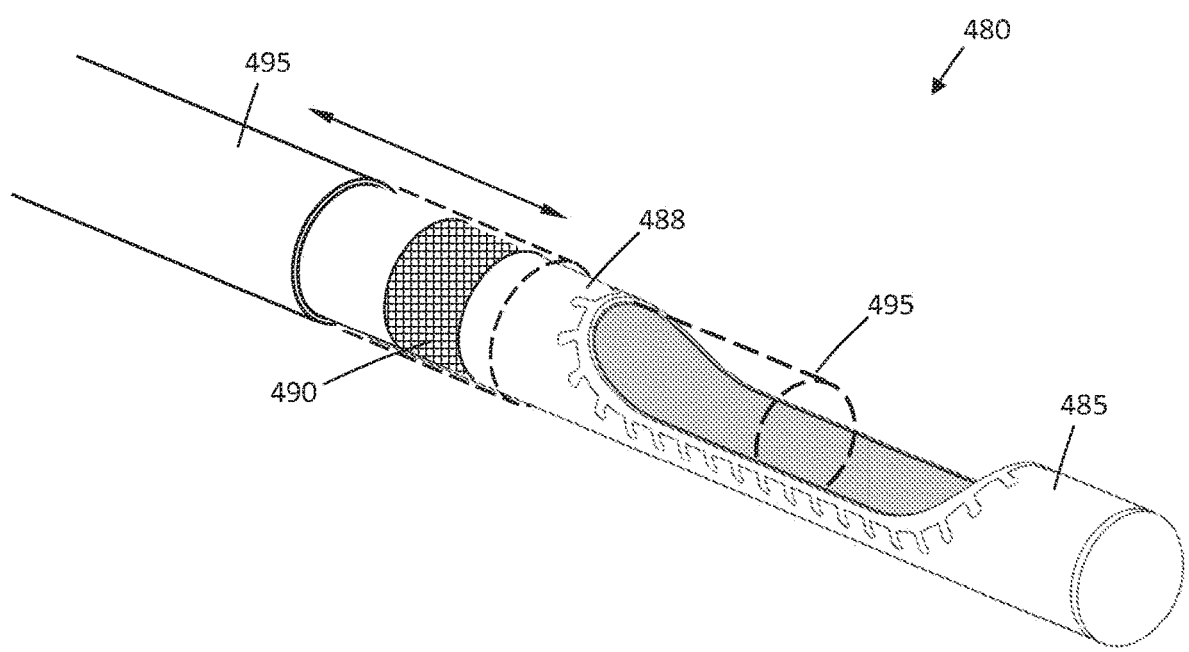
FIG. 19 is a view of another variation of working end similar to that of FIGS. 16A-16C showing an alternative electrode arrangement.

FIG. 19 illustrates another working end 480 that is similar to the embodiments described previously. In one variation, the exterior of the outer sleeve 485 is covered with a thin film dielectric material 488 except for the electrode region indicated at 490. This embodiment further comprises slidable outer sleeve 495 of a substantially rigid dielectric material that can be moved over electrode 490. Thus, the exterior electrode 490 can be completely exposed, partly exposed or completely covered. In one aspect the invention, by covering the exterior electrode 490, the system can be made to operate only with an RF current path between the distal cutting electrode 460 and an internal electrode surface of outer sleeve 485 as described in previous embodiments. In one variation, the inner cutting sleeve 495 may operate optimally to more effectively achieve explosive vaporization of saline in the distal end chamber as the inner cutting sleeve 495 approaches the distal end of its stroke, in performing the tissue-extraction function described in relation to FIGS. 12A-12C.

In another aspect of the invention, a method of cutting tissue comprises providing an elongated probe comprising a windowed outer sleeve and an inner sleeve that is reciprocatable to cut tissue in the window, wherein a distal edge of the inner sleeve comprises a first polarity RF cutting electrode configured for plasma formation thereabout, manipulating the window into and out of contact with tissue in a saline environment while reciprocating the inner sleeve and RF cutting electrode, and delivering RF energy at system operational parameters such that a plasma is formed at the RF cutting electrode only when in contact with tissue. It has been found that maintaining a fluid outflow cools the RF electrode and prevents vaporization and plasma formation. When the electrode contacts tissue, the fluid flow about the electrode is impeded and plasma ignition occurs instantly. A negative pressure source as described above can provide a selected saline flow rate configured to prevent plasma formation about the RF cutting electrode when not in contact with tissue.

While the above embodiments relate to reciprocating cutting sleeves, an electrosurgical tissue cutting probe can also be configured with an inner cutting sleeve that moveable axially and/or rotationally to cut tissue.

It should be appreciated that while an RF source is suitable for causing explosive vaporization of the captured fluid volume, any other energy source can be used and falls within the scope of the invention, such as an ultrasound transducer, HIFU, a laser or light energy source, a microwave or a resistive heat source.

In another embodiment, the probe can be configured with a lumen in communication with a remote liquid source to deliver fluid to the interior chamber 240.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of resecting tissue with electrosurgical energy, comprising:
    inserting an elongated probe into a body cavity, the elongated probe comprising:
        an outer sleeve having a window extending through a side wall of the outer sleeve at a location between a proximal end and a distal end of the outer sleeve;
        an inner sleeve that is reciprocatable to resect tissue in the window, wherein a distal edge of the inner sleeve comprises a first polarity RF electrode configured for plasma formation thereabout;
        wherein the outer sleeve comprises a second polarity RF electrode; and
        a slidable dielectric sleeve disposed around the outer sleeve;
    manipulating the window into and out of contact with tissue in a saline environment while reciprocating the inner sleeve; and
    delivering RF energy from the first polarity RF electrode to the second polarity RF electrode while reciprocating the inner sleeve to resect tissue extending into the window.

2. The method of claim 1, wherein the outer sleeve comprises a metallic material.

3. The method of claim 2, further comprising:
    sliding the dielectric sleeve partially over the second polarity RF electrode to reduce an exposed surface area of the second polarity RF electrode.

4. The method of claim 2, wherein an exterior surface of the outer sleeve is covered with a thin-film dielectric material except for the second polarity RF electrode.

5. The method of claim 4, further comprising:
    sliding the dielectric sleeve completely over the second polarity RF electrode;
    wherein subsequently delivering RF energy causes current flow between the first polarity RF electrode and an interior surface of the outer sleeve.

6. The method of claim 5, wherein current flow between the first polarity RF electrode and the interior surface of the outer sleeve when the inner sleeve is in a window-closed configuration causes explosive vaporization of saline disposed within the inner sleeve.

7. The method of claim 1, wherein the second polarity RF electrode faces radially outward.

8. The method of claim 7, further comprising:
    sliding the dielectric sleeve over the second polarity RF electrode to adjust an exposed surface area of the second polarity RF electrode.

9. The method of claim 1, further comprising:
    actuating a negative pressure source in communication with a proximal end of a lumen in the inner sleeve thereby causing a flow of saline through the lumen.

10. A method of resecting tissue with electrosurgical energy, comprising:
    distending a body cavity with saline;
    inserting an elongated probe into the body cavity, the elongated probe comprising:
        a metallic outer sleeve having a tissue-receiving window extending through a side wall of the metallic outer sleeve at a location between a proximal end and a distal end of the metallic outer sleeve;
        an inner sleeve that is reciprocatable within the metallic outer sleeve, wherein a distal end of the inner sleeve includes a first polarity RF electrode movable across the tissue-receiving window to resect tissue in the tissue-receiving window;
        wherein the metallic outer sleeve includes a second polarity RF electrode; and
        a rigid dielectric sleeve slidably disposed about the metallic outer sleeve;

manipulating the window into and out of contact with tissue in the distended body cavity while reciprocating the first polarity RF electrode across the tissue-receiving window; and delivering RF energy from the first polarity RF electrode to the second polarity RF electrode while reciprocating the first polarity RF electrode across the tissue-receiving window to resect tissue extending into the window.

11. The method of claim 10, further comprising:

actuating a negative pressure source in communication with a proximal end of a lumen in the inner sleeve thereby causing a flow of saline through the lumen.

12. The method of claim 10, further comprising:

sliding the dielectric sleeve over the outer sleeve to adjust an exposed surface area of the second polarity RF electrode.

13. The method of claim 10, wherein the outer sleeve includes a thin film dielectric material disposed on an exterior surface of the outer sleeve.

14. The method of claim 13, wherein an exposed portion of the exterior surface of the outer sleeve is the second polarity RF electrode.

15. The method of claim 14, further comprising:

sliding the dielectric sleeve over the exposed portion of the exterior surface of the outer sleeve to adjust an exposed surface area of the second polarity RF electrode.

16. The method of claim 14, further comprising:

sliding the dielectric sleeve completely over the second polarity RF electrode;

wherein subsequently delivering RF energy causes current flow between the first polarity RF electrode and an interior surface of the outer sleeve.

17. The method of claim 16, wherein current flow between the first polarity RF electrode and the interior surface of the outer sleeve when the inner sleeve is in a window-closed configuration causes explosive vaporization of saline disposed within the inner sleeve adjacent the distal end of the metallic outer sleeve.

18. The method of claim 10, further comprising a dielectric material extending around a perimeter of the tissue-receiving window.

19. The method of claim 18, wherein the second polarity RF electrode is disposed proximal of the dielectric material extending around the perimeter of the tissue-receiving window.

20. The method of claim 10, wherein the first polarity RF electrode is a ring electrode, and wherein plasma is formed at a distal edge thereof when delivering RF energy.

* * * * *